United States Patent
Jones et al.

(10) Patent No.: US 10,221,686 B2
(45) Date of Patent: Mar. 5, 2019

(54) MEASURING AN ADSORBING CHEMICAL IN DOWNHOLE FLUIDS

(75) Inventors: Christopher M. Jones, Houston, TX (US); Michael T. Pelletier, Houston, TX (US); Mark Proett, Missouri City, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 14/344,842

(22) PCT Filed: Sep. 13, 2011

(86) PCT No.: PCT/US2011/051420
§ 371 (c)(1),
(2), (4) Date: Mar. 13, 2014

(87) PCT Pub. No.: WO2013/039485
PCT Pub. Date: Mar. 21, 2013

(65) Prior Publication Data
US 2014/0338900 A1 Nov. 20, 2014

(51) Int. Cl.
| | | |
|---|---|---|
| *E21B 49/00* | (2006.01) | |
| *E21B 49/08* | (2006.01) | |
| *E21B 49/10* | (2006.01) | |
| *G01N 33/00* | (2006.01) | |
| *G01N 1/18* | (2006.01) | |
| *G01N 1/14* | (2006.01) | |
| *G01N 1/20* | (2006.01) | |

(52) U.S. Cl.
CPC ............ *E21B 49/086* (2013.01); *E21B 49/00* (2013.01); *E21B 49/10* (2013.01); *G01N 1/18* (2013.01); *G01N 33/0044* (2013.01); *G01N 2001/1454* (2013.01); *G01N 2001/2071* (2013.01)

(58) Field of Classification Search
CPC ........ E21B 49/00; E21B 47/00; E21B 49/086; E21B 49/10; G01N 33/0044
USPC .......................................................... 703/10
See application file for complete search history.

(56) References Cited

U.S. PATENT DOCUMENTS

| | | | |
|---|---|---|---|
| 4,278,128 A | 7/1981 | Satter et al. | |
| 4,344,142 A * | 8/1982 | Diehr, II | ............. B29C 35/0288 264/325 |
| 5,723,781 A * | 3/1998 | Pruett | ..................... E21B 47/01 250/260 |

(Continued)

OTHER PUBLICATIONS

Feng et al., Adsorption of Hydrogen Sulfied onto Activated Carbon Fibers: Effect of Pore Structure and Surface Chemistry, 2005, Enviromental science and technology, doi:10.1021/es0507158, p. 9744-9749.*

(Continued)

*Primary Examiner* — Stephanie E Bloss
*Assistant Examiner* — Mohammad K Islam
(74) *Attorney, Agent, or Firm* — Haynes and Boone, LLP

(57) ABSTRACT

Interaction of adsorbing chemicals with a downhole tool presents inaccuracies in the adsorbing chemical measurement and analysis. The principles of the present disclosure provide a method and system of sampling fluids including an adsorbing chemical in a subterranean reservoir. One method may include modeling an interaction between the adsorbing chemical and a downhole tool, applying the model to a measurement of the adsorbing chemical, and adjusting the measurement in response to applying the model.

31 Claims, 25 Drawing Sheets

(56) References Cited

U.S. PATENT DOCUMENTS

| | | | |
|---|---|---|---|
| 6,176,323 B1 | 1/2001 | Weirich et al. | |
| 6,214,175 B1 | 4/2001 | Heinemann et al. | |
| 6,349,766 B1* | 2/2002 | Bussear | E21B 33/127 166/113 |
| 6,939,717 B2 | 9/2005 | Jiang et al. | |
| 7,025,138 B2* | 4/2006 | Kurkjian | E21B 49/081 166/113 |
| 7,027,968 B2 | 4/2006 | Jiang et al. | |
| 7,353,869 B2 | 4/2008 | Wetzel et al. | |
| 8,037,935 B2* | 10/2011 | Pelletier | E21B 49/10 166/100 |
| 8,631,864 B2* | 1/2014 | Saenger | E21B 17/1064 166/241.2 |
| 2001/0023614 A1 | 9/2001 | Tubel et al. | |
| 2002/0194906 A1* | 12/2002 | Goodwin | E21B 49/08 73/152.46 |
| 2003/0032562 A1* | 2/2003 | Crossman | C08L 3/00 507/212 |
| 2003/0035895 A1 | 2/2003 | Bianchi et al. | |
| 2003/0139916 A1 | 7/2003 | Choe et al. | |
| 2004/0043501 A1 | 3/2004 | Means et al. | |
| 2005/0205256 A1 | 9/2005 | DiFoggio | |
| 2005/0269499 A1 | 12/2005 | Jones et al. | |
| 2005/0270023 A1 | 12/2005 | Freedman | |
| 2006/0032301 A1 | 2/2006 | DiFoggio | |
| 2006/0272809 A1 | 12/2006 | Tubel et al. | |
| 2007/0119244 A1* | 5/2007 | Goodwin | E21B 47/10 73/152.28 |
| 2007/0143023 A1* | 6/2007 | Betancourt | E21B 49/08 702/11 |
| 2008/0087427 A1 | 4/2008 | Kaminsky et al. | |
| 2008/0110253 A1* | 5/2008 | Stephenson | E21B 49/005 73/152.19 |
| 2008/0141826 A1 | 6/2008 | Marya et al. | |
| 2008/0160626 A1* | 7/2008 | Hoots | C23F 11/00 436/102 |
| 2008/0190180 A1* | 8/2008 | Zougari | G01N 33/2823 73/61.62 |
| 2009/0182541 A1* | 7/2009 | Crick | E21B 43/00 703/10 |
| 2009/0317916 A1* | 12/2009 | Ewing | G01N 1/2214 436/153 |
| 2009/0324337 A1* | 12/2009 | Ball | G01N 33/24 405/128.25 |
| 2010/0025110 A1 | 2/2010 | John et al. | |
| 2010/0116046 A1* | 5/2010 | Martin | E21B 49/081 73/152.23 |
| 2011/0011157 A1* | 1/2011 | Bourlon | B01J 20/205 73/23.41 |
| 2011/0061945 A1* | 3/2011 | Saenger | E21B 17/1085 175/434 |
| 2011/0266056 A1* | 11/2011 | Pop | E21B 49/08 175/50 |
| 2011/0282584 A1* | 11/2011 | Baez | E21B 49/00 702/13 |
| 2012/0027658 A1* | 2/2012 | Karwacki | B01D 53/864 423/247 |
| 2012/0053838 A1* | 3/2012 | Andrews | E21B 49/082 702/8 |
| 2012/0138364 A1* | 6/2012 | Leonard | G01N 27/026 175/50 |
| 2012/0285178 A1* | 11/2012 | Pennewitz | E21B 36/001 62/3.1 |

OTHER PUBLICATIONS

Kun-Lin et al., The Effect of Trace Amount of H2S on Co2 Corrosion Investigated by Using the EIS technique, 2005, NACE, Corrosion 2005 05630, p. 1-16.*

Kane, Roles of H2s in the Behaviour of Engineering Alloys, 1998, NACE, Corrosion98 274, p. 1-28.*

Smith, Control of corrosion in oil and gas production, 1999, ISSN 0007-0599, British Corrosion Journal 199 vol. 34 No. 4, p. 247-253.*

*Alice* vs *CLS Bank*, Supreme Court Decision, 2013.*

International Search Report and Written Opinion, dated May 1, 2012, for International Patent Application No. PCT/US2011/051420.

* cited by examiner

MEASURING AN ADSORBING CHEMICAL IN DOWNHOLE FLUIDS

CROSS-REFERENCE TO RELATED APPLICATIONS

This application is the U.S. National Stage under 35 U.S.C. § 371 of International Patent Application No. PCT/US2011/051420 filed Sep. 13, 2011, and entitled "Measuring an Adsorbing Chemical in Downhole Fluids" which is hereby incorporated by reference in its entirety.

BACKGROUND

During the drilling and completion of oil and gas wells, it may be necessary to engage in ancillary operations, such as evaluating the production capabilities of formations intersected by the wellbore. For example, after a well or well interval has been drilled, zones of interest are often tested or sampled to determine various formation properties such as permeability, fluid type, fluid quality, formation temperature, formation pressure, bubblepoint and formation pressure gradient. These tests are performed in order to determine whether commercial exploitation of the intersected formations is viable and how to optimize production. The acquisition of accurate data from the wellbore is critical to the optimization of hydrocarbon wells. This wellbore data can be used to determine the location and quality of hydrocarbon reserves, whether the reserves can be produced through the wellbore, and for well control during drilling operations.

Frequently, adsorbing chemicals or corrosive substances occur in the hydrocarbon reservoirs. Adsorption is the adhesion of molecules (as gases, solutes, or liquids) in a thin layer to the surface of a solid or liquid. Thus, an adsorbing chemical is a gas, liquid, solute, or suspension that is attracted to and held by the surface of a solid or other liquid. Desorption is to removed by reverse adsorption, or the release of the molecules from the solid or liquid surface.

For example, Hydrogen Sulfide ($H_2S$) may be present as the result of reactions involving sulfur containing materials such as Kerogen or Anhydride ($CaSO_4$), or as the result of the reaction between anaerobic bacteria and organic matter in the reservoir. The resulting levels of $H_2S$ can vary, with an exemplary range being 5 to 40 percent concentration. $H_2S$ is problematic for several reasons. It is a health hazard. $H_2S$ is also corrosive to drilling and production equipment. $H_2S$ can react with downhole equipment and the formation to produce scale, which then impedes or closes off the production flow line or the permeability of the formation. Steps taken to address these known problems with $H_2S$ and other corrosive substances increase the overall cost of drilling and production. Further, $H_2S$ containing hydrocarbons (sour oil) is less valuable than hydrocarbons without $H_2S$ (sweet oil). While $H_2S$ is an exemplary corrosive, adsorbing chemical, other adsorbing chemicals can similarly affect downhole operations and production.

Different levels of $H_2S$ in the petroleum reservoir dictate different levels of $H_2S$ mitigation and different valuations of the oil. To properly project the economics and well plan, the level of $H_2S$ in the reservoir must be accurately known.

To obtain downhole concentration levels of $H_2S$, the formation is tested or sampled for the level of $H_2S$ therein. A formation tester or other measurement device is placed in the borehole to test or capture a sample of fluid from the formation. In some cases, the formation tester directly measures $H_2S$ optically, electrically, or chemically. In other cases, the formation tester receives and captures a fluid sample for analysis in the tool or subsequently at the surface of the well. The formation tester may be conveyed downhole a number of ways. The tool may be used in conjunction with wireline logging operations or as a component of a logging-while-drilling (LWD) or measurement-while-drilling (MWD) package. In wireline logging operations, the drill string is removed from the wellbore and measurement tools are lowered into the wellbore using a heavy cable (wireline) that includes wires for providing power and control from the surface. In LWD and MWD operations, the measurement tools are integrated into the drill string and are ordinarily powered by batteries and controlled by either on-board or remote control systems. With LWD/MWD testers, the testing equipment is subject to harsh conditions in the wellbore during the drilling process that can damage and degrade the formation testing equipment before and during the testing process. These harsh conditions include vibration and torque from the drill bit, exposure to drilling mud, drilled cuttings, and formation fluids, hydraulic forces of the circulating drilling mud, high downhole temperatures, and scraping of the formation testing equipment against the sides of the wellbore. Sensitive electronics and sensors must be robust enough to withstand the pressures and temperatures, and especially the extreme vibration and shock conditions of the drilling environment, yet maintain accuracy, repeatability, and reliability.

Regardless of the testing tool configuration, interaction of adsorbing chemicals with the tool presents inaccuracies in the adsorbing chemical measurement and analysis, as described more fully herein. The principles of the present disclosure overcome the limitations of the prior art in accurately measuring adsorbing or corrosive chemicals such as $H_2S$.

BRIEF DESCRIPTION OF THE DRAWINGS

For a detailed description of exemplary embodiments of the invention, reference will now be made to the accompanying drawings in which.

DETAILED DESCRIPTION

Figure 1:
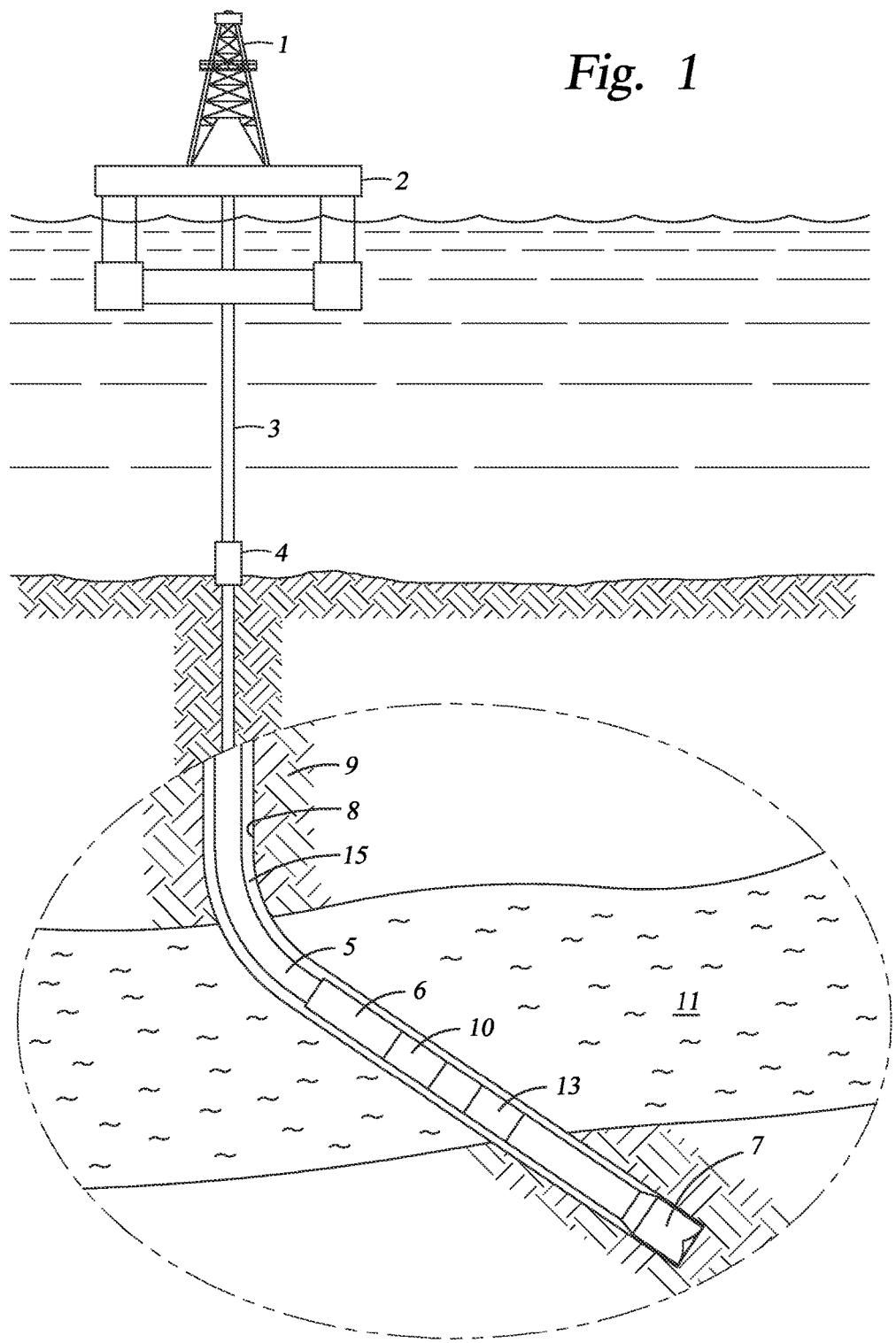
FIG. 1 is a schematic view, partly in cross-section, of a drilling apparatus with a formation tester.

In the drawings and description that follow, like parts are typically marked throughout the specification and drawings with the same reference numerals. The drawing figures are not necessarily to scale. Certain features of the disclosure may be shown exaggerated in scale or in somewhat schematic form and some details of conventional elements may not be shown in the interest of clarity and conciseness. The present disclosure is susceptible to embodiments of different forms. Specific embodiments are described in detail and are shown in the drawings, with the understanding that the present disclosure is to be considered an exemplification of the principles of the disclosure, and is not intended to limit the disclosure to that illustrated and described herein. It is to be fully recognized that the different teachings of the embodiments discussed below may be employed separately or in any suitable combination to produce desired results.

In the following discussion and in the claims, the terms "including" and "comprising" are used in an open-ended fashion, and thus should be interpreted to mean "including, but not limited to . . . ". Unless otherwise specified, any use of any form of the terms "connect", "engage", "couple", "attach", or any other term describing an interaction between elements is not meant to limit the interaction to direct interaction between the elements and may also include indirect interaction between the elements described. Reference to up or down will be made for purposes of description with "up", "upper", "upwardly" or "upstream" meaning toward the surface of the well and with "down", "lower", "downwardly" or "downstream" meaning toward the terminal end of the well, regardless of the well bore orientation. In addition, in the discussion and claims that follow, it may be sometimes stated that certain components or elements are in fluid communication. By this it is meant that the components are constructed and interrelated such that a fluid could be communicated between them, as via a passageway, tube, or conduit. Also, the designation "MWD" or "LWD" are used to mean all generic measurement while drilling or logging while drilling apparatus and systems. The various characteristics mentioned above, as well as other features and characteristics described in more detail below, will be readily apparent to those skilled in the art upon reading the following detailed description of the embodiments, and by referring to the accompanying drawings.

Referring initially to FIG. 1, a drilling apparatus including a formation tester is shown. A formation tester 10 is shown enlarged and schematically as a part of a bottom hole assembly 6 including a sub 13 and a drill bit 7 at its distal most end. The bottom hole assembly 6 is lowered from a drilling platform 2, such as a ship or other conventional land platform, via a drill string 5. The drill string 5 is disposed through a riser 3 and a well head 4. Conventional drilling equipment (not shown) is supported within a derrick 1 and rotates the drill string 5 and the drill bit 7, causing the bit 7 to form a borehole 8 through formation material 9. The drill bit 7 may also be rotated using other means, such as a downhole motor. The borehole 8 penetrates subterranean zones or reservoirs, such as reservoir 11, that are believed to contain hydrocarbons in a commercially viable quantity. An annulus 15 is formed thereby. In addition to the formation tester 10, the bottom hole assembly 6 contains various conventional apparatus and systems, such as a down hole drill motor, a rotary steerable tool, a mud pulse telemetry system, MWD or LWD sensors and systems, a processor and electronic storage media, and others known in the art.

Figure 2:
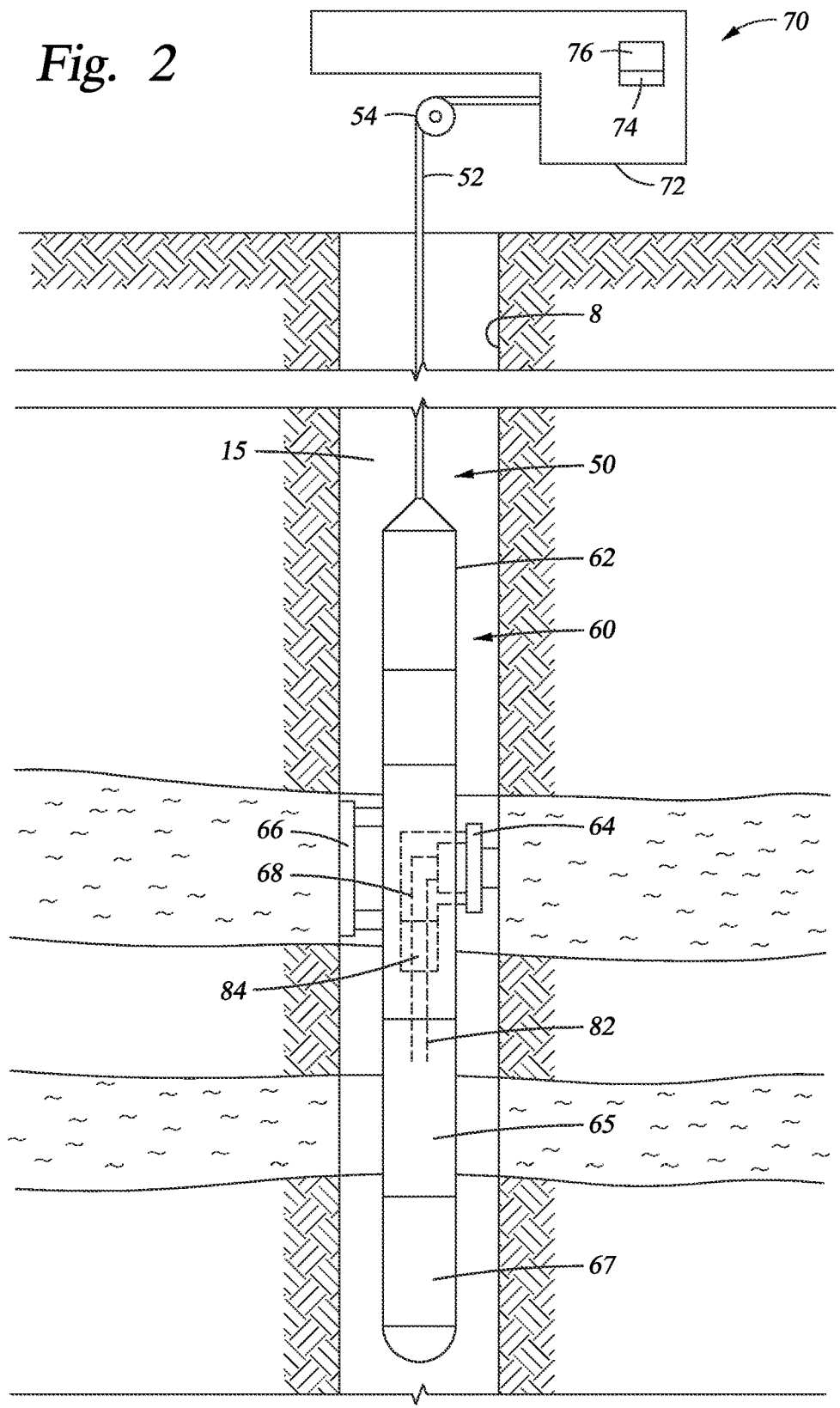
FIG. 2 is a schematic view, partly in cross-section, of a formation tester conveyed by wireline.

In some embodiments, and with reference to FIG. 2, a formation testing tool 60 is disposed on a tool string 50 conveyed into the borehole 8 by a cable 52 and a winch 54. The testing tool includes a body 62, a sampling assembly 64, a backup assembly 66, analysis modules 68, 84 including electronic devices, a flowline 82, a battery module 65, and an electronics module 67. The formation tester 60 is coupled to a surface unit 70 that may include an electrical control system 72 having an electronic storage medium 74 and a control processor 76. In other embodiments, the tool 60 may alternatively or additionally include an electrical control system, an electronic storage medium and a processor.

Figure 3:
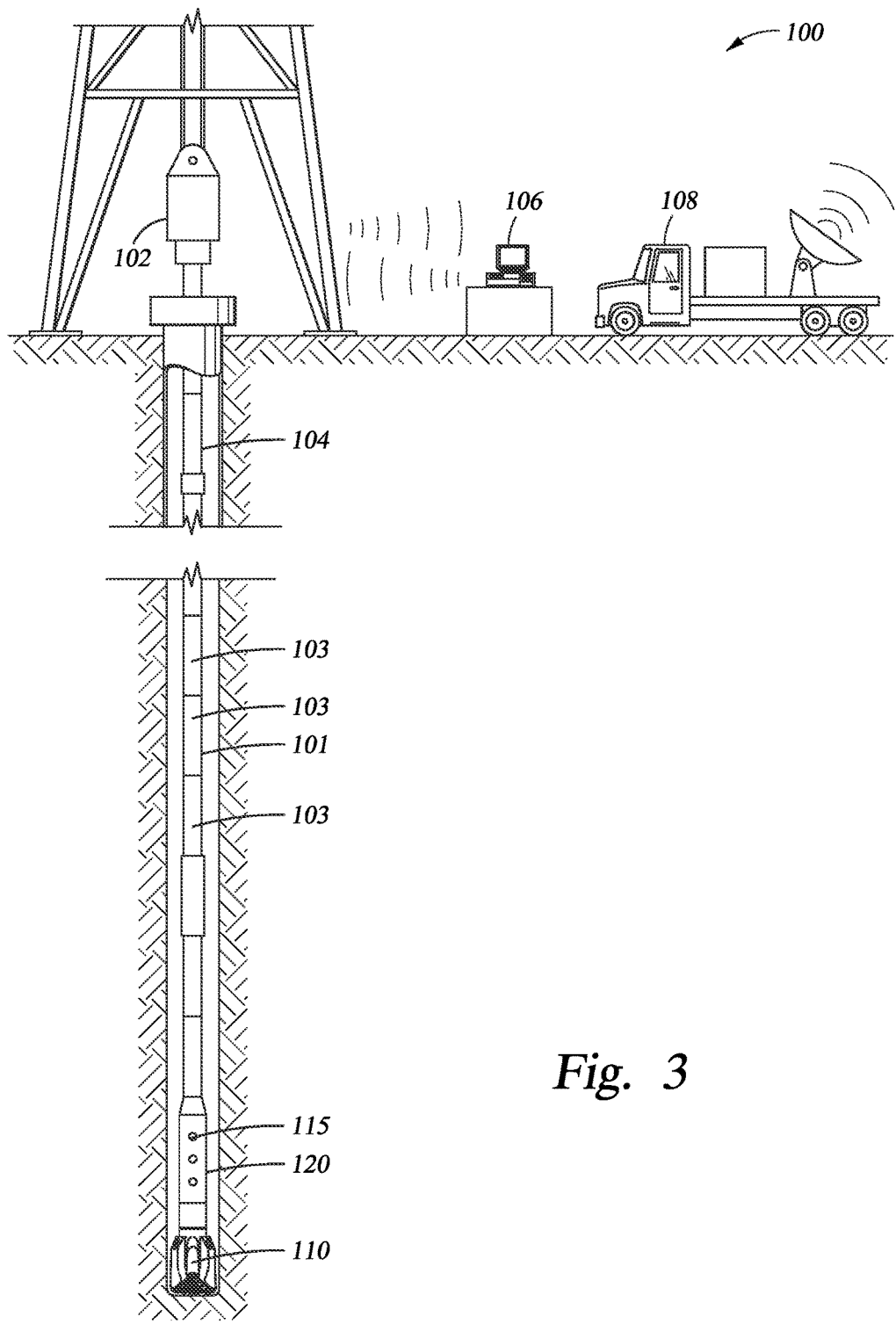
FIG. 3 is a schematic view, partly in cross-section, of a formation tester disposed on a wired drill pipe connected to a telemetry network.

Referring to FIG. 3, a telemetry network 100 is shown. A formation tester 120 is coupled to a drill string 101 formed by a series of wired drill pipes 103 connected for communication across junctions using communication elements. It will be appreciated that work string 101 can be other forms of conveyance, such as wired coiled tubing. The downhole drilling and control operations are interfaced with the rest of the world in the network 100 via a top-hole repeater unit 102, a kelly 104 or top-hole drive (or, a transition sub with two communication elements), a computer 106 in the rig control center, and an uplink 108. The computer 106 can act as a server, controlling access to network 100 transmissions, sending control and command signals downhole, and receiving and processing information sent up-hole. Thus, the processor can be located in the computer 106. The software running the server can control access to the network 100 and can communicate this information via dedicated land lines, satellite uplink 108), Internet, or other means to a central server accessible from anywhere in the world. The formation tester 120 is shown linked into the network 100 just above the drill bit 110 for communication along its conductor path and along the wired drill string 101. The processor in computer 106 can be used to communicate with and process information from the formation tester 120, or a processor may be located in the formation tester 106 or adjacent the formation tester 106 in the surrounding components of the drill string 101.

The formation tester 120 may include a plurality of transducers 115 disposed on the formation tester 120 to relay downhole information to the operator at surface or to a remote site. The transducers 115 may include any conventional source/sensor (e.g., pressure, temperature, gravity, etc.) to provide the operator with formation and/or borehole parameters, as well as diagnostics or position indication relating to the tool. The telemetry network 100 may combine multiple signal conveyance formats (e.g., mud pulse, fiber-optics, acoustic, EM hops, etc.). It will also be appreciated that software/firmware may be configured into the formation tester 120 and/or the network 100 (e.g., at surface, downhole, in combination, and/or remotely via wireless links tied to the network).

Figure 4:
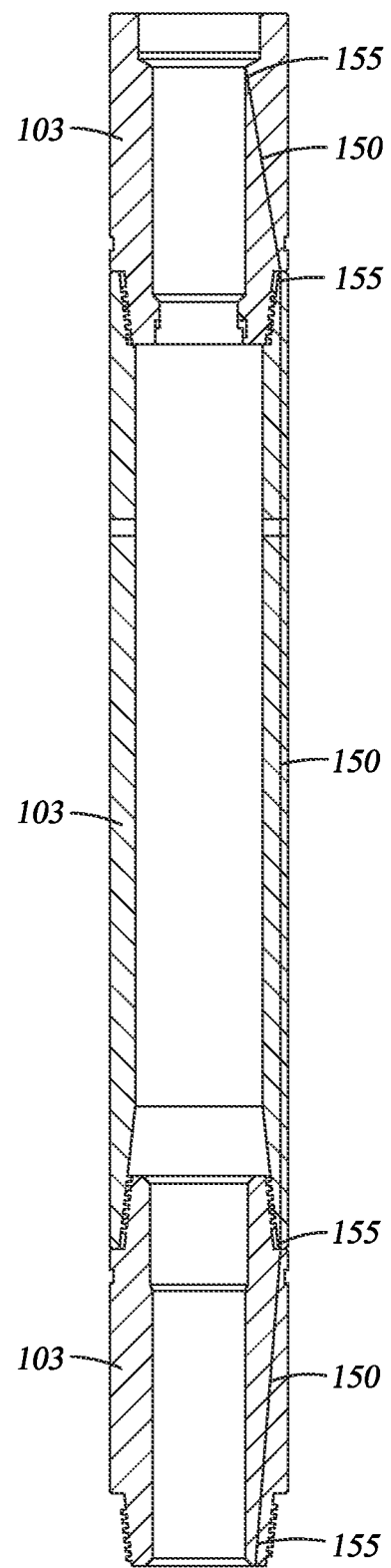
FIG. 4 is a cross-section view of a section of wired drill pipe.

Referring briefly to FIG. 4, sections of wired drill pipe 103 are enlarged for clarity. The wired drill pipe 103 includes conductors 150 that traverse the entire length of the pipe sections. Communication elements 155 allow the transfer of power and/or data between the pipe sections 103. A data/power signal may be transmitted along a pipe section of the wired drill string, such as the pipe section with formation tester 120 (FIG. 3), from one end through the conductor(s)

150 to the other end across the communication elements 155. In some embodiments, the conductor(s) 150 comprise coaxial cables, copper wires, optical fiber cables, triaxial cables, and twisted pairs of wire. The conductor(s) 150 may be disposed through a hole formed in the walls of the outer tubular members of the pipes 103. The communication elements 155 may comprise inductive couplers, direct electrical contacts, optical couplers, and combinations thereof. Portions of the wired drill pipes 103 may be subs or other connections means. The ends of subs or connections means of the wired subs 103 are configured to communicate within the downhole telemetry network 100.

Figure 5:
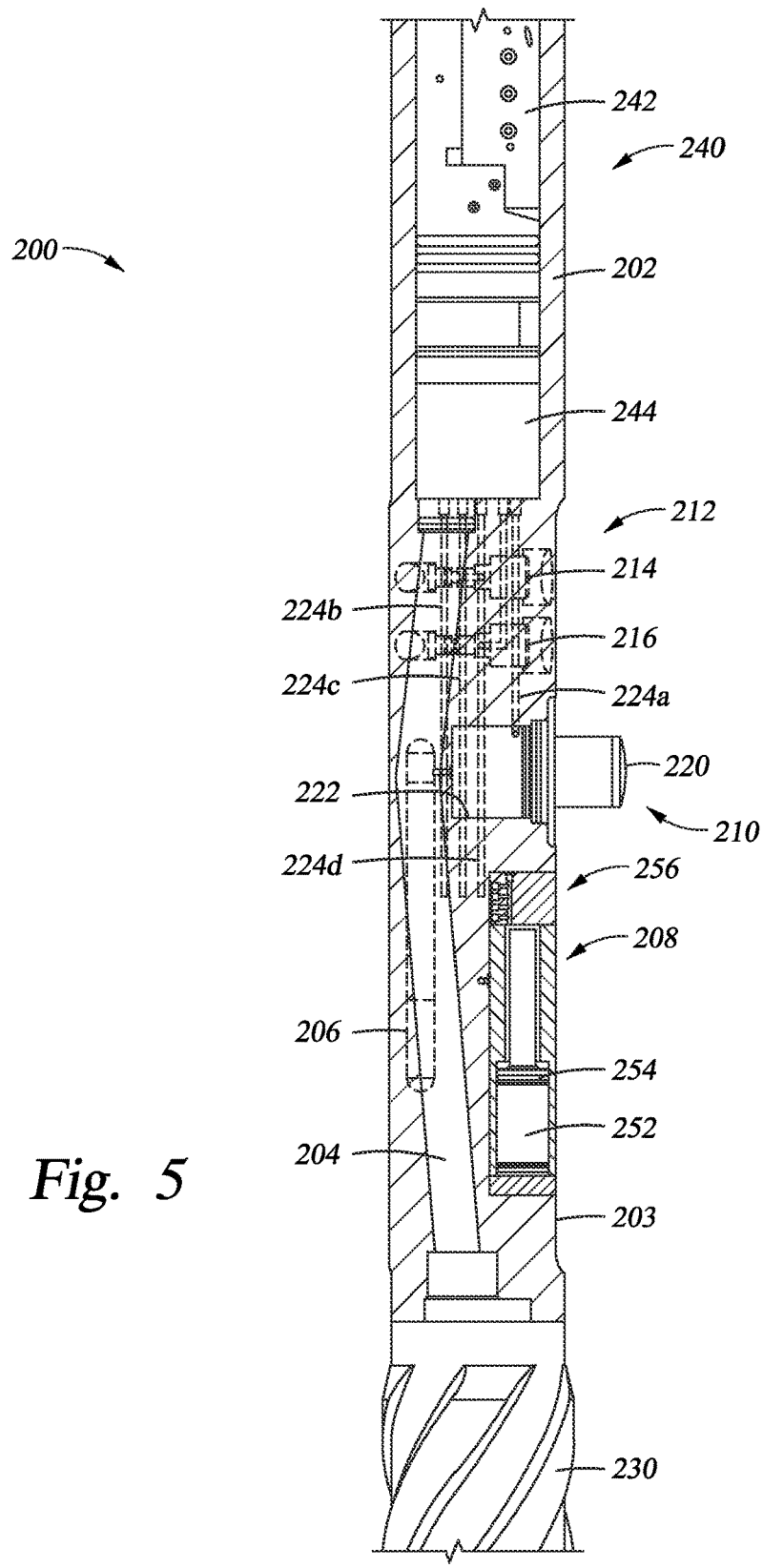
FIG. 5 is a side view, partly in cross-section, of a drill collar including a formation probe assembly.

Referring next to FIG. 5, an embodiment of an MWD formation probe collar section 200 is shown in detail, which may be used as the tool 10 in FIG. 1 or the tool 120 in FIG. 3. A drill collar 202 houses the formation tester or probe assembly 210. The probe assembly 210 includes various components for operation of the probe assembly 210 to receive and analyze formation fluids from the earth formation 9 and the reservoir 11. An extendable probe member 220 is disposed in an aperture 222 in the drill collar 202 and extendable beyond the drill collar 202 outer surface, as shown. The probe member 220 is retractable to a position recessed beneath the drill collar 202 outer surface. The probe assembly 210 may include a recessed outer portion 203 of the drill collar 202 outer surface adjacent the probe member 220. The probe assembly 210 includes a draw down or piston accumulator assembly 208, a sensor 206, a valve assembly 212 having a flow line shutoff valve 214 and equalizer valve 216, and a drilling fluid flow bore 204. At one end of the probe collar 200, generally the lower end when the tool 10 is disposed in the borehole 8, is an optional stabilizer 230, and at the other end is an assembly 240 including a hydraulic system 242 and a manifold 244.

The piston assembly 208 includes a piston chamber 252 containing a piston 254 and a manifold 256 including various fluid and electrical conduits and control devices. The piston assembly 208, the probe 220, the sensor 206 (e.g., a pressure gauge) and the valve assembly 212 communicate with each other and various other components of the probe collar 200, such as the manifold 244 and hydraulic system 242, as well as the tool 10 via conduits 224a, 224b, 224c and 224d. The conduits 224a, 224b, 224c, 224d include various fluid flow lines and electrical conduits for operation of the probe assembly 210 and probe collar 200.

Figure 6:
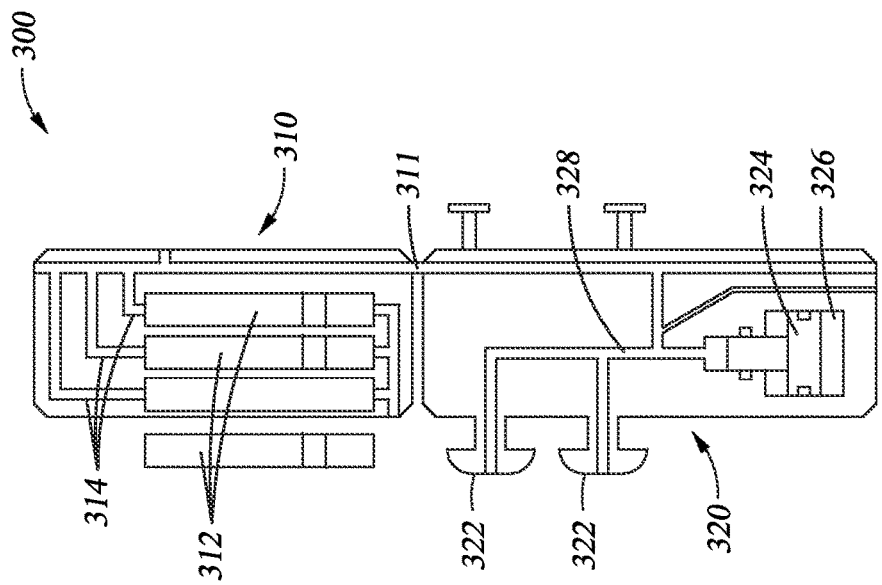
FIG. 6 is a schematic view of a formation tester surrounded by well fluids having an adsorbing chemical.
Figure 6:
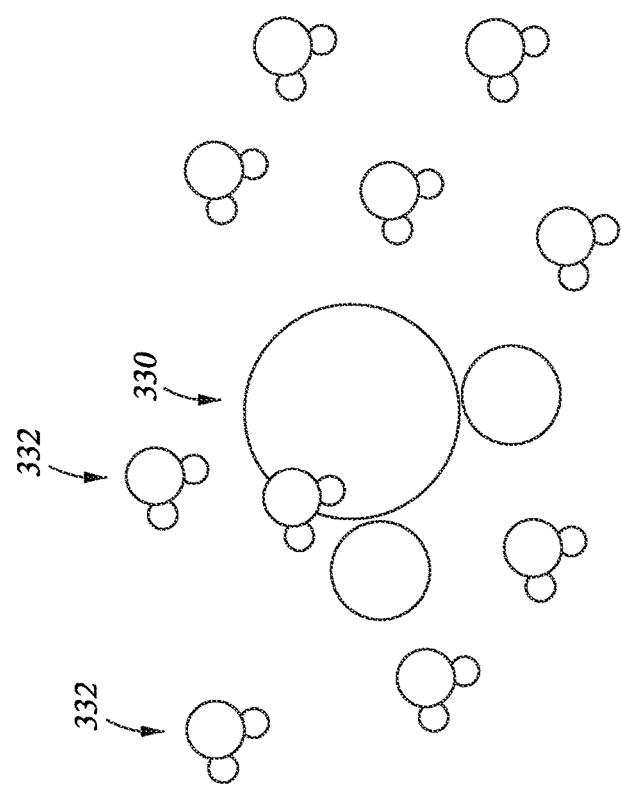
Figure 7:
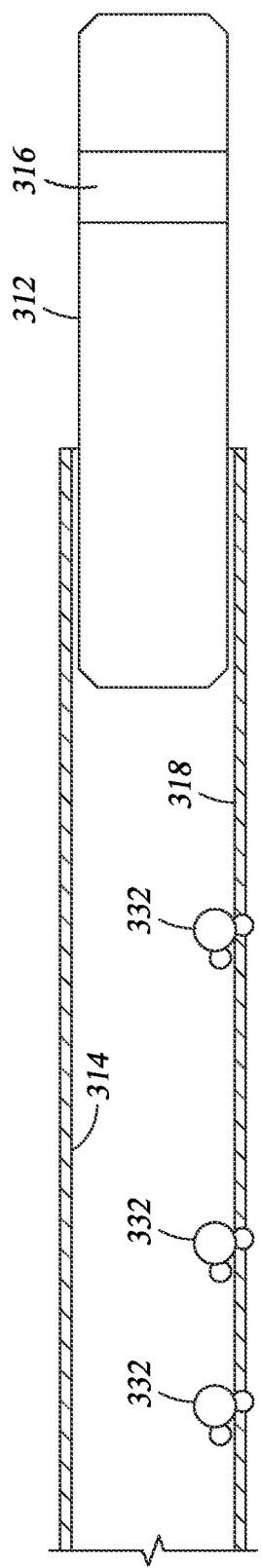
FIG. 7 is an enlarged view of a sample chamber and fluid passageway of the formation tester of FIG. 6, interacting with the adsorbing chemical.

In the various tool configurations described above, and in other similar tools for measuring or capturing formation fluids with adsorbing or corrosive chemicals, the adsorbing chemical interacts and reacts with the tool itself. Referring to FIGS. 6 and 7, a formation tester 300 includes a sample module 310 and a probe module 320. The formation tester 300 is surrounded by a well fluid 330 including adsorbing chemical molecules 332. The formation tester 300 is actuated to engage a drawdown piston 324 in a cylinder 326 to flow the well fluids 330 into probes 322 and a fluid passageway 328. The probe module 320 is coupled to the sample module 310, and fluidicly coupled by a passageway 311, such that the well fluids 330 also flow through fluid passageways 314 to sample bottles 312 with pistons 316. As the well fluids 330 flow through the passageway 314, as shown in FIG. 7, the chemical molecules 332 adsorb to the inner surface 318. The chemical molecules 318 will also adsorb to other surfaces of the formation tester 300 to which contact is made. Similarly, the chemical molecules will desorb from the surface 318 and other inner surfaces of the formation tester 300 after the primary well fluid 330 has dissipated form the passageways 314 and other parts of the formation tester 300.

Figure 8:
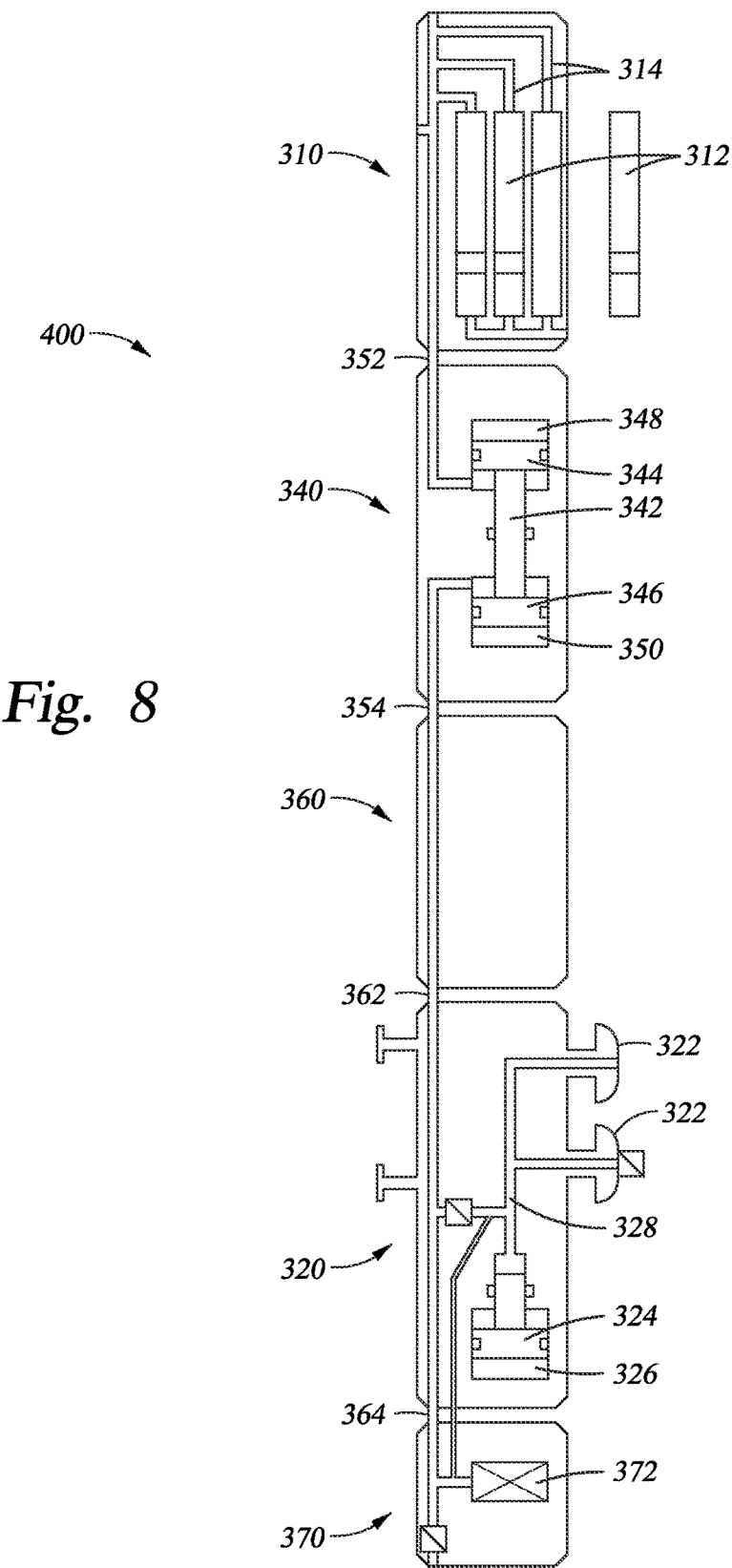
FIG. 8 is a schematic view of another configuration of a formation tester.

The formation tester may include further configurations, such as the formation tester 400 of FIG. 8. The sample module 310 is coupled to a hydraulic pump module 340, with a fluidic coupling via a passageway 352. A hydraulic power module 360 is coupled between the hydraulic pump module 340 and the probe module 320, and includes a fluid passageway with fluidic couplings 354, 362. A pressure gauge module or sub 370 is coupled to the probe module 320, including a fluidic coupling 364 to provide fluids to a pressure gauge 372.

Other formation tester configurations are also possible by removing or re-arranging the above-noted tool modules, with exemplary embodiments described in more detail below. Changes to the formation tester configuration are often in response to the specifications of a particular well operation or well plan. Consequently, the adsorbing chemical interaction characteristics relative to the formation tester also change, thereby adversely affecting measurements and detected concentration levels of the adsorbing chemical. The formation tester may also be other types of downhole tools that are exposed to well fluids having adsorbing chemicals.

As previously noted, $H_2S$ is an exemplary adsorbing chemical and will be used for purposes of description. The actual concentration of $H_2S$ in a pristine reservoir fluid is changed by tool interaction and resulting adsorption before the $H_2S$ measurement is taken in the tool or at the surface. If the fluid sample is captured in a sampling chamber, the $H_2S$ may also react with the sampling chamber. The resulting $H_2S$ measurement is not representative of the $H_2S$ concentration within the reservoir itself. Typically, the $H_2S$-tool interaction decreases the concentration of $H_2S$ and results in measurements that underestimate the amount of $H_2S$ in a reservoir.

Figure 9:
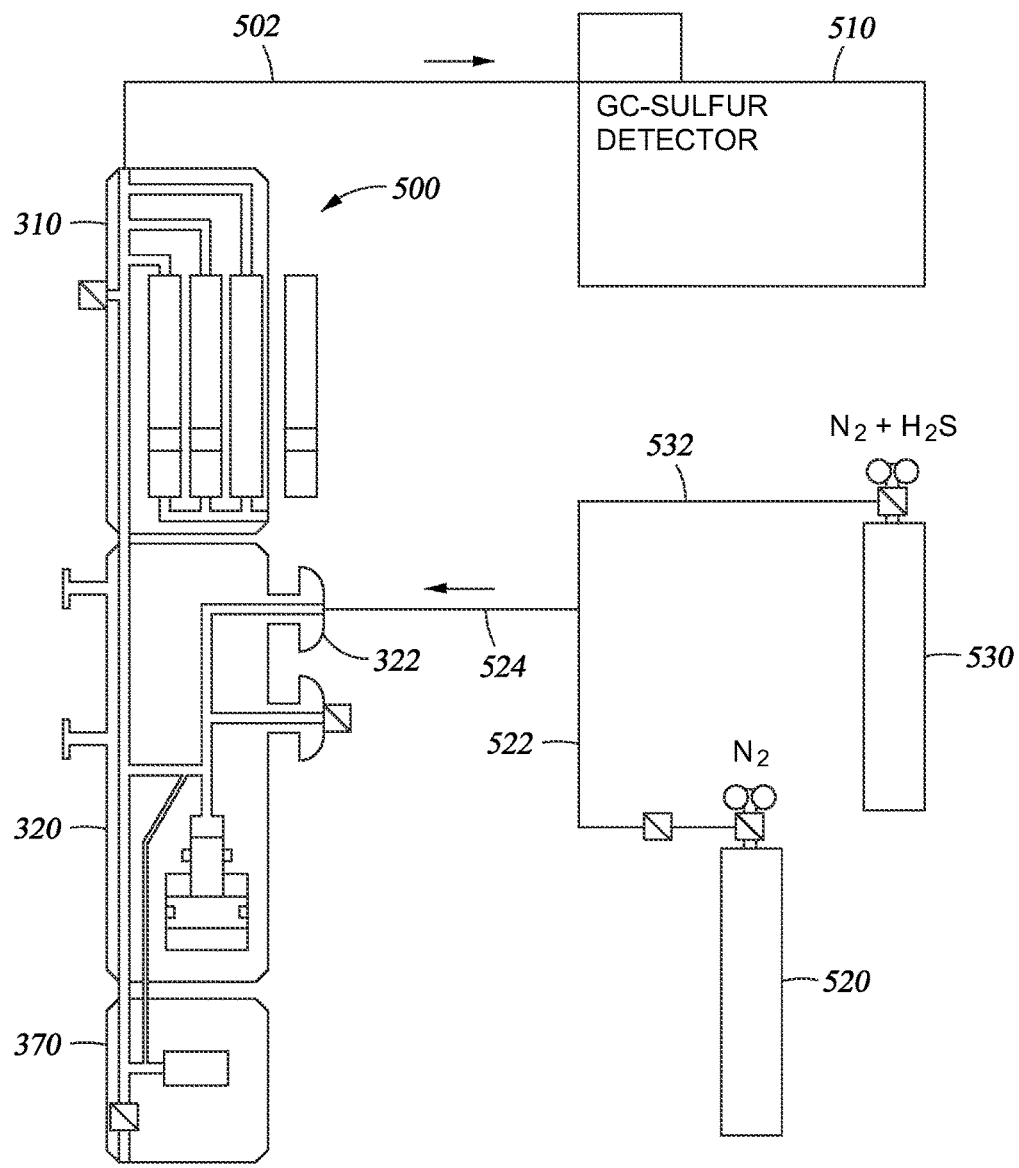
FIG. 9 is a schematic view of still another configuration of a formation tester coupled to a test apparatus.
Figure 10:
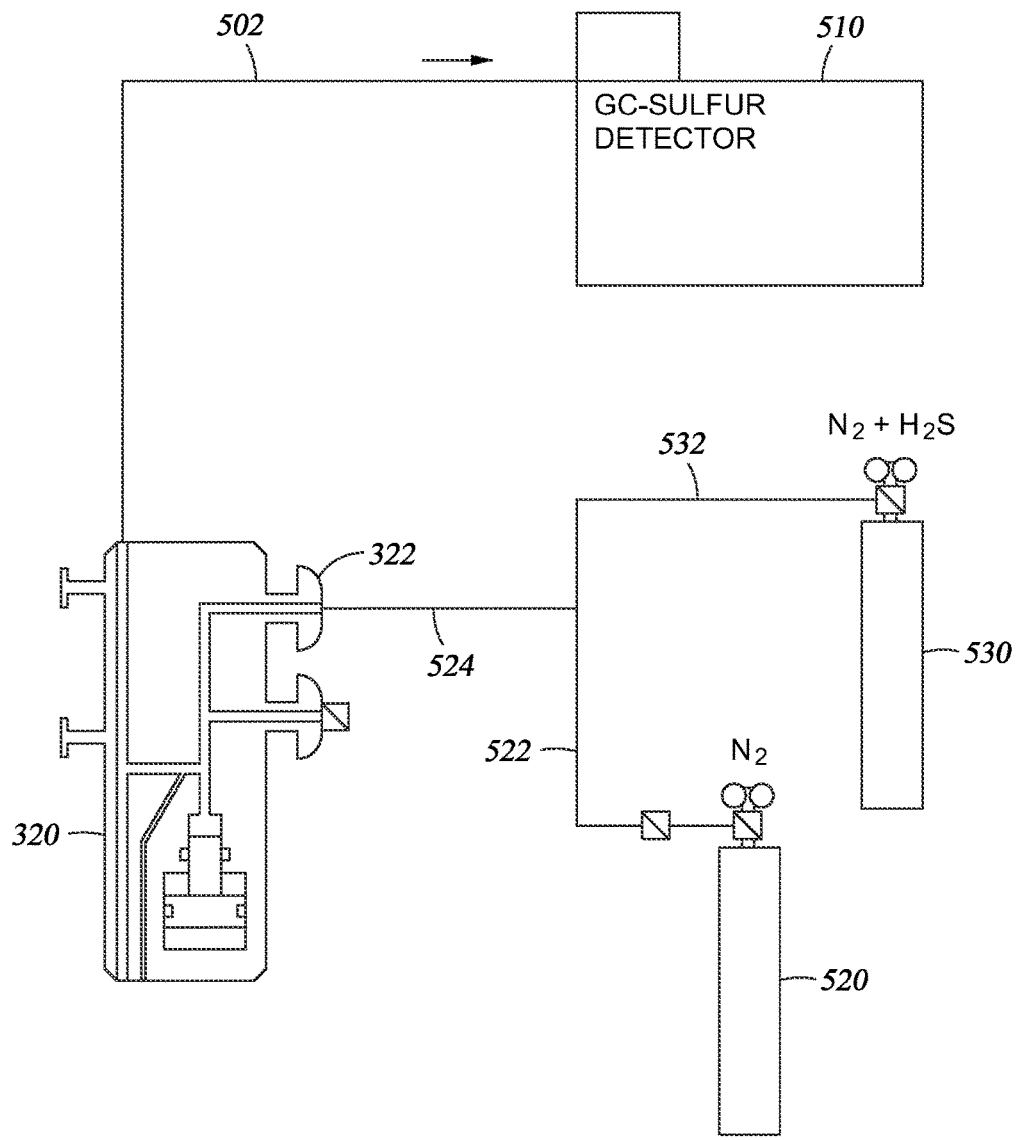
FIG. 10 is a schematic view of a further configuration of a formation tester coupled to the test apparatus.

A series of downhole formation tester modules and tool assemblies can be tested for $H_2S$ interaction. A dry nitrogen gas laced with low levels of $H_2S$ is flowed through the tools, and adsorption and subsequent desorption measurements are taken. The dry nitrogen gas laced with $H_2S$ is an exemplary corrosive fluid with adsorbing chemicals, and it was chosen because it is an anhydrous binary mixture that represents a worst-case slow adsorption rate. Exemplary test tools include a downhole multiple sample chamber section, such as sample module 310, coupled to a dual probe/pad assembly section, such as probe module 320, and a quartz gauge section, such as pressure gauge module 370, represented as a formation tester 500 in FIG. 9. The formation tester 500 is coupled to a test apparatus including a sulfur detector 510, such as a gas chromatograph, and a nitrogen supply 520 and a nitrogen plus $H_2S$ supply 530. Supply lines 522, 532 couple into a fluid passageway 524 directing fluids into the probe 322. In additional test embodiments, only the probe module 320 is connected to the test apparatus of FIG. 9, as shown in FIG. 10. Similarly, only the pressure gauge module 370 may be connected to the test apparatus, or only the sample bottle or chamber of the sample module 310. In further test embodiments, the sample module 310 is coupled to the probe module 320, represented as formation tester 600 in FIG. 11. The formation tester 600 is coupled to the test apparatus including the sulfur detector 510 and the nitrogen and nitrogen plus $H_2S$ supplies 520, 530. Supply lines 522, 532 couple into the fluid passageway 524 directing fluids into the probe 322. In still additional embodiments, formation tester configurations include a nuclear magnetic resonance (NMR) fluid identification and contamination section, and/or a hydraulic flushing pump section, such as the hydraulic pump module 340.

Exemplary test conditions for the various formation tester configurations include temperatures of approximately 75° F. to 176° F., pressures of approximately 20 psi to 80 psi, flow rates of approximately 20 to 190 cc/min, $H_2S$ parts per million (ppm) of approximately 210 to 217 in nitrogen, and a time of approximately 10 hours to 48 hours. The various formation testers can be subjected to the $H_2S$-containing abrasive fluids under these approximate conditions, though these conditions may vary according to need and desired objectives. In some embodiments, the flow of the $H_2S$-containing abrasive fluids is equivalent to one to five years of field usage. Data is collected on the formation tester response to the $H_2S$-containing abrasive fluid flow.

As will be described in detail below, a finite element steady-state model is developed to express the adsorption and desorption of $H_2S$ onto the individual formation tester modules and tool assemblies, then compared against the testing data. The developed finite element model predicts the general behavior of the adsorption-desorption of $H_2S$ relative to the various geometries of the formation tester configurations herein. Additionally, the model is used to understand the effect of different tool parameters on steady state behavior. Data from the model is used to generate adsorption and desorption curves for history matching to the observed experimental behavior. The resultant $H_2S$ simulator is configurable for real tool geometries including multiple module or tool sections coupled together, as will be understood from the detailed explanation below.

Figure 11:
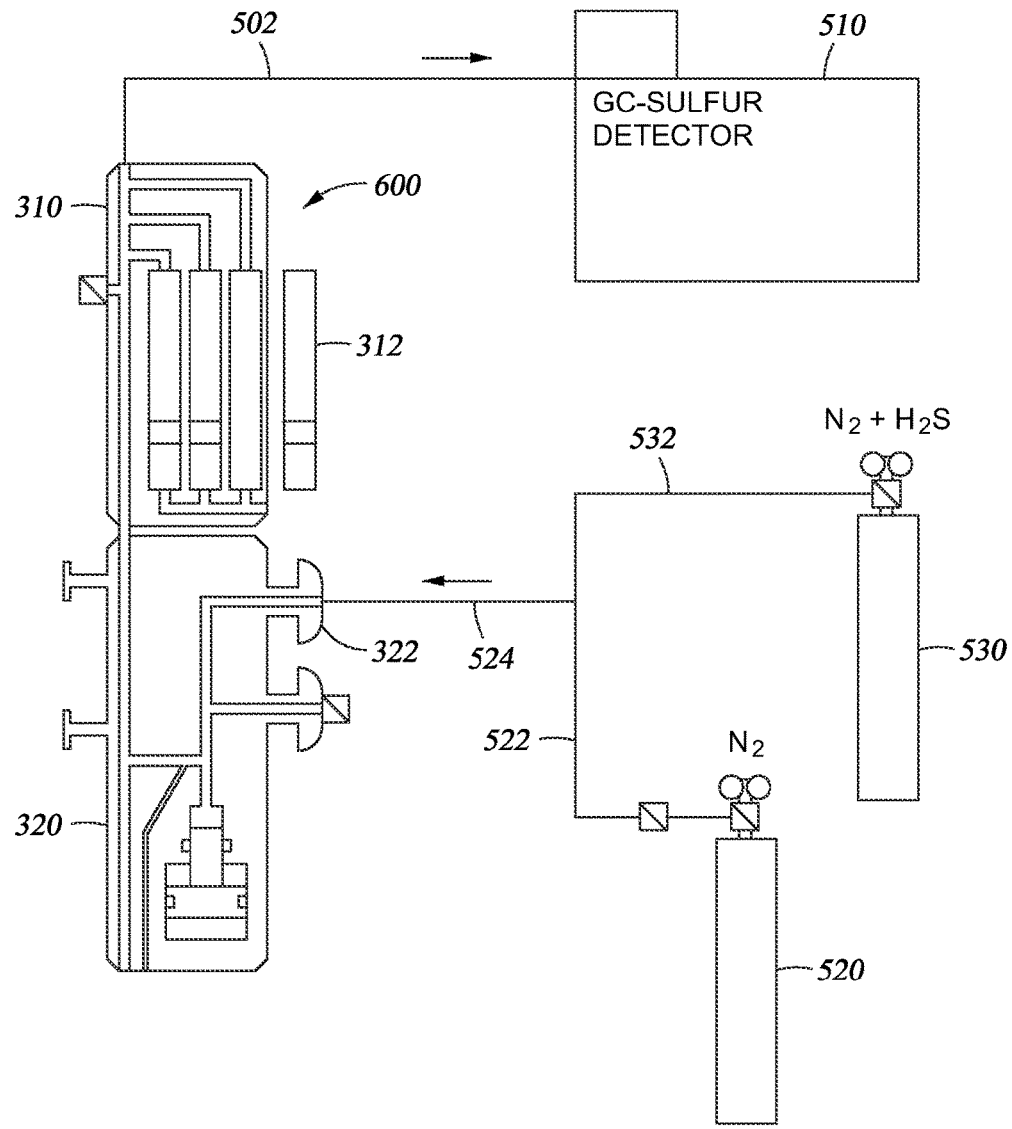
FIG. 11 is a schematic view of a yet another configuration of a formation tester coupled to the test apparatus.
Figure 12:
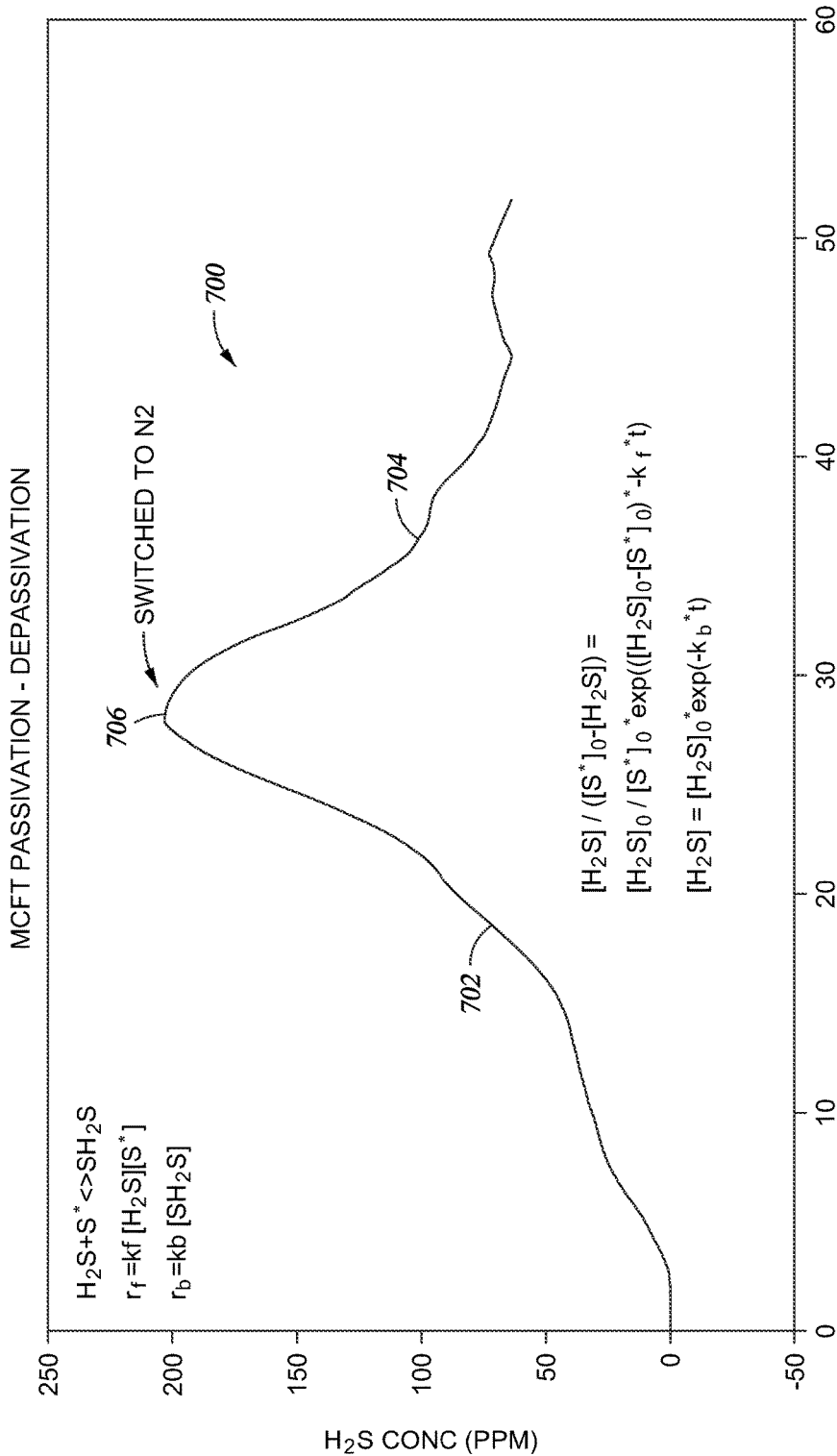
FIGS. 12-21 show plots and graphs representing data gathering and finite element analysis for actual measurements of an adsorbing chemical and a simulation of the adsorption-desorption curve for the adsorbing chemical.
Figure 13:
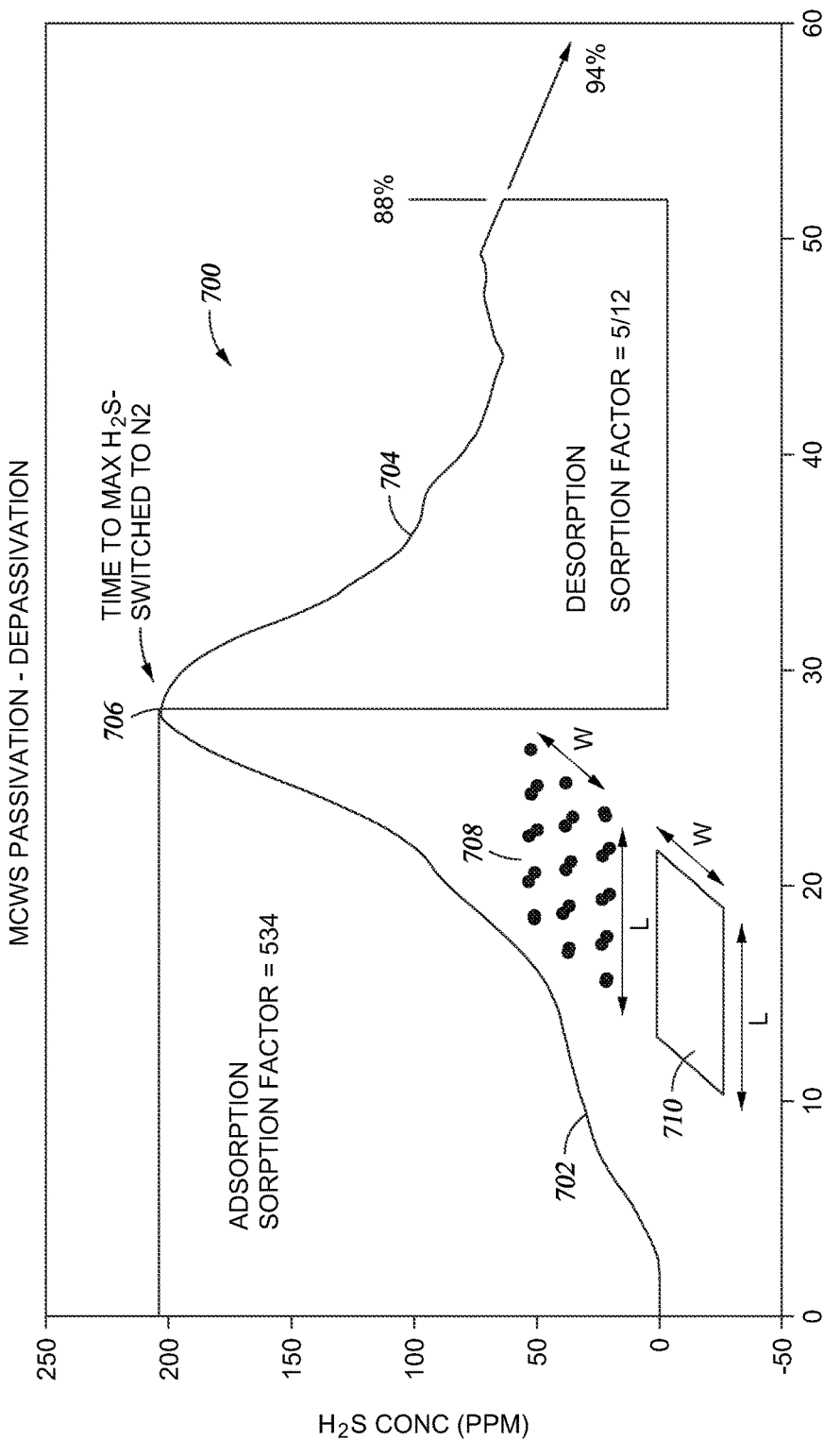
Figure 14:
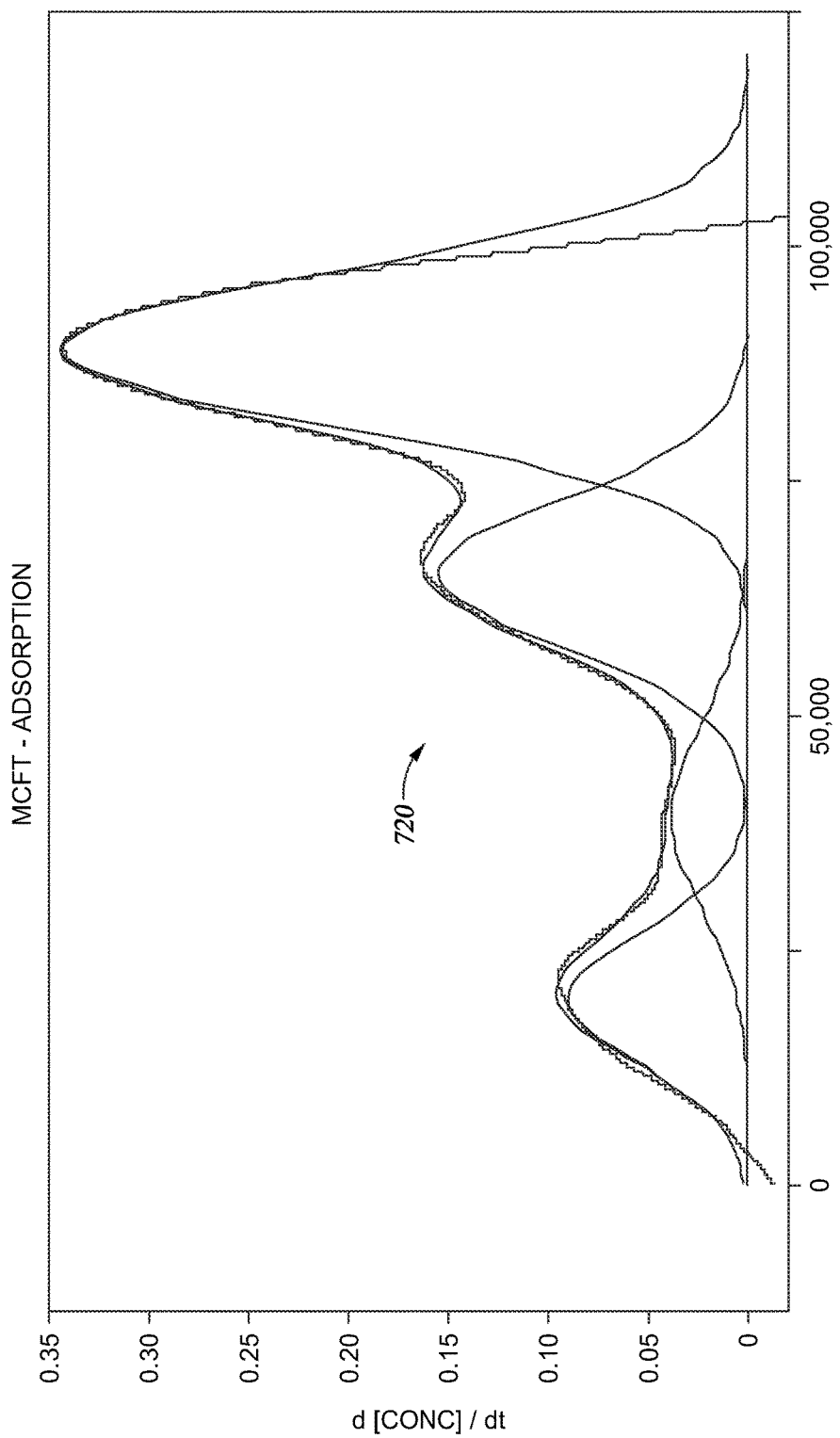
Figure 15:
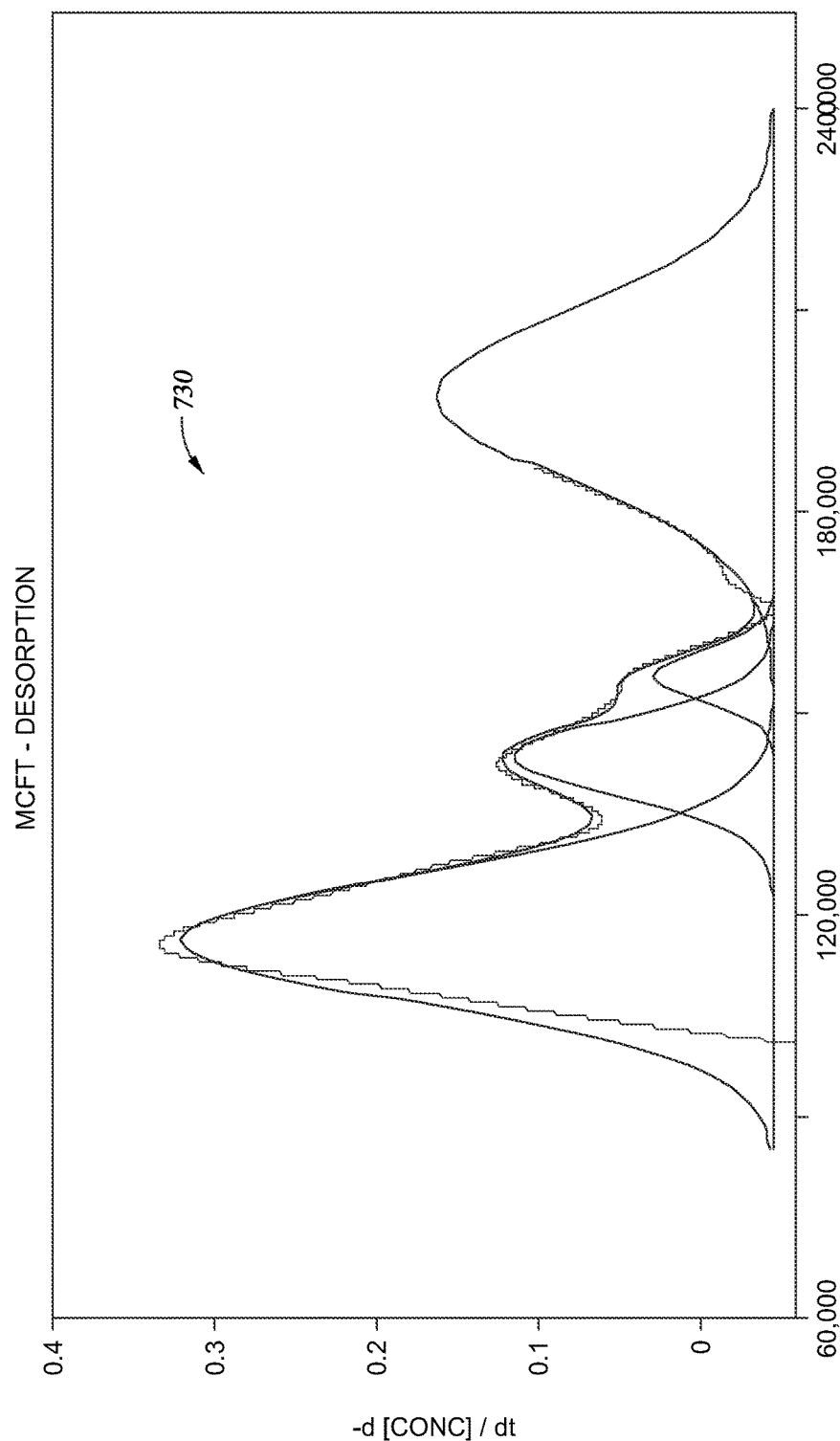
Figure 16:
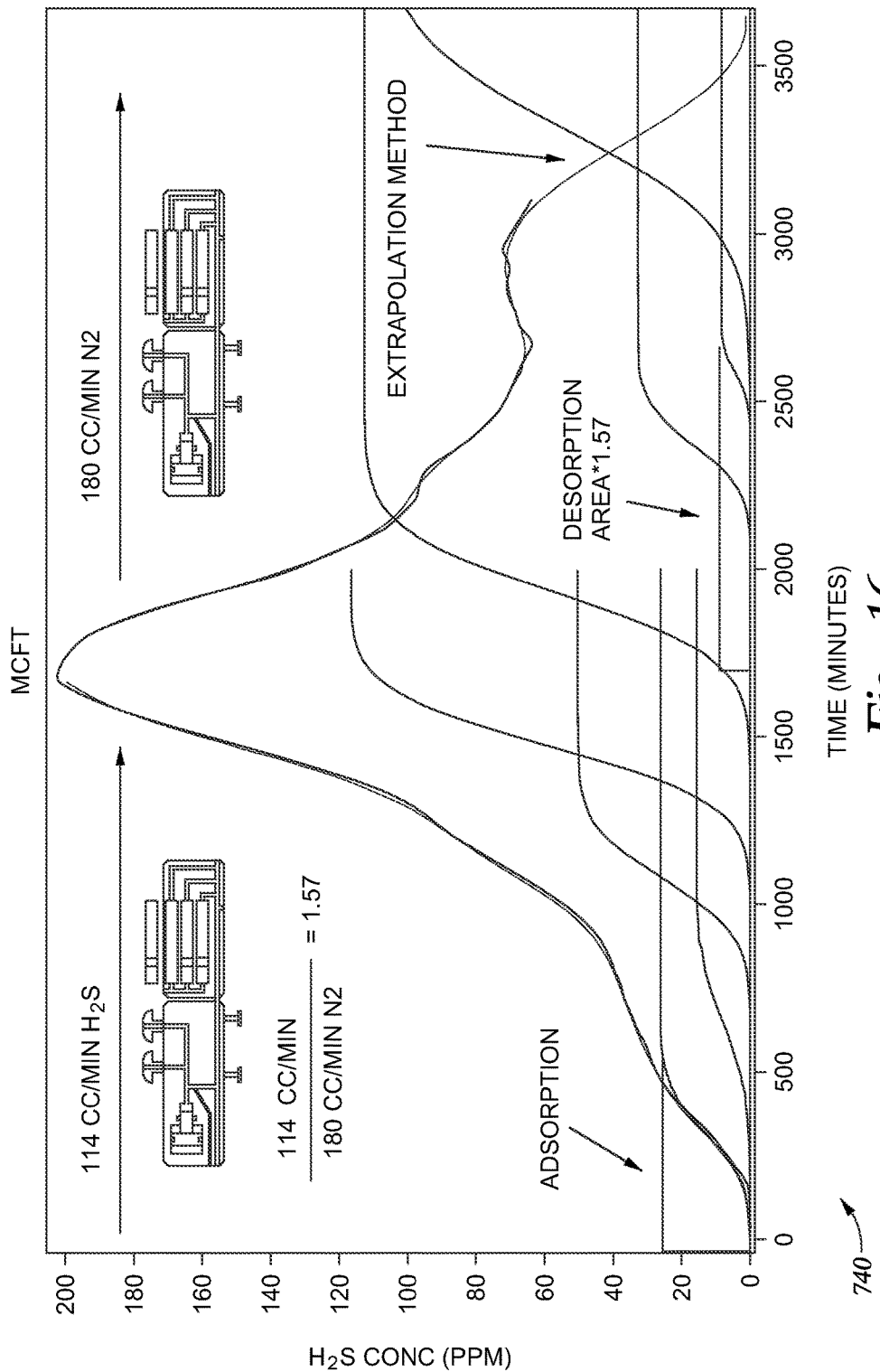
Figure 17:
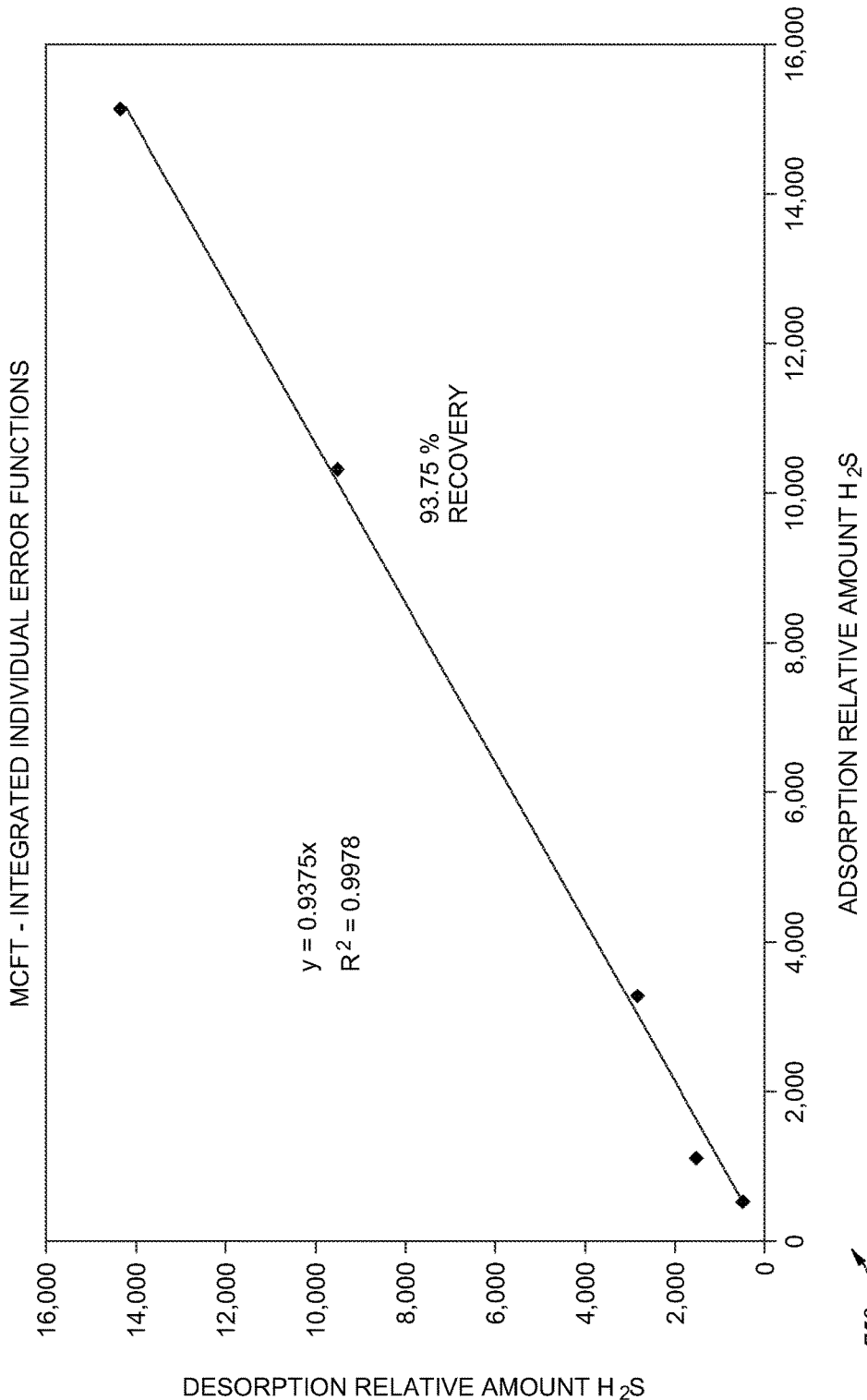

In an exemplary test, the formation tester 600, also called a minimum configuration formation tester (MCFT), is subjected to the test flow of nitrogen plus $H_2S$ as depicted in FIG. 11. The $H_2S$ adsorption and desorption (or, passivation and depassivation, respectively) profile for the formation tester 600 is recorded with $H_2S$ concentration in ppm given as a function of time, represented by plot 700 in FIG. 12. A curve 702 shows the adsorption of $H_2S$ to the formation tester 600, and the curve 704 shows the corresponding desorption from the formation tester 600 after a switch 706 from nitrogen plus $H_2S$ to just nitrogen. With reference now to FIG. 13, additional analysis shows a 94% recovery of $H_2S$ after desorption, with sorption factors of 534 and 5/12, for the $H_2S$ molecules 708 relative to the formation tester surface 710. With reference to FIG. 14, the finite element analysis includes a first derivative plot 720 of the $H_2S$ adsorption profile 702. Similarly, FIG. 15 includes a plot 730 of a first derivative of the $H_2S$ desorption profile 704. The integrated adsorption and desorption analyses are shown with the graph 740 of FIG. 16, and the graph 750 of FIG. 17 including Gaussians integrated individual error functions.

Figure 18:
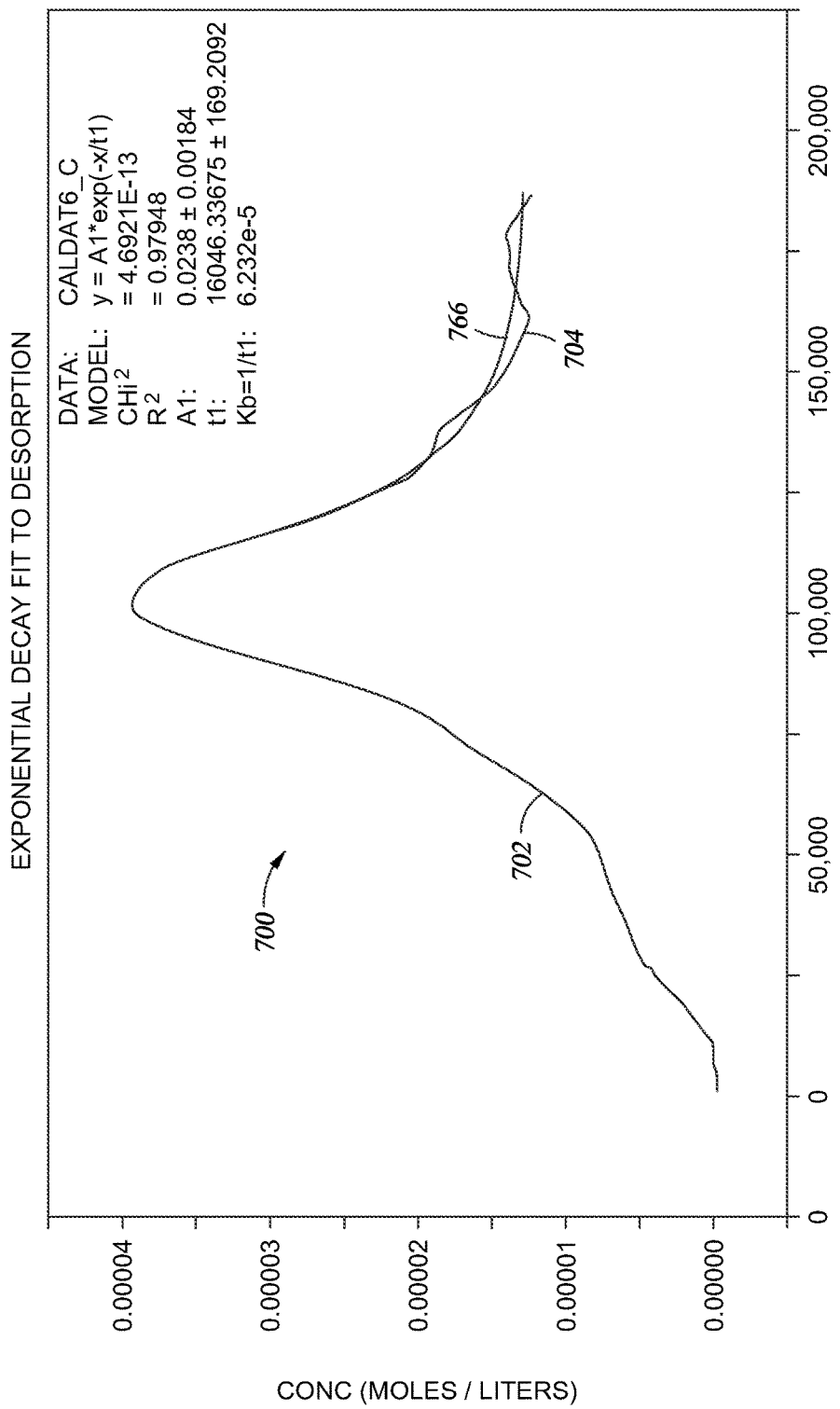
Figure 19:
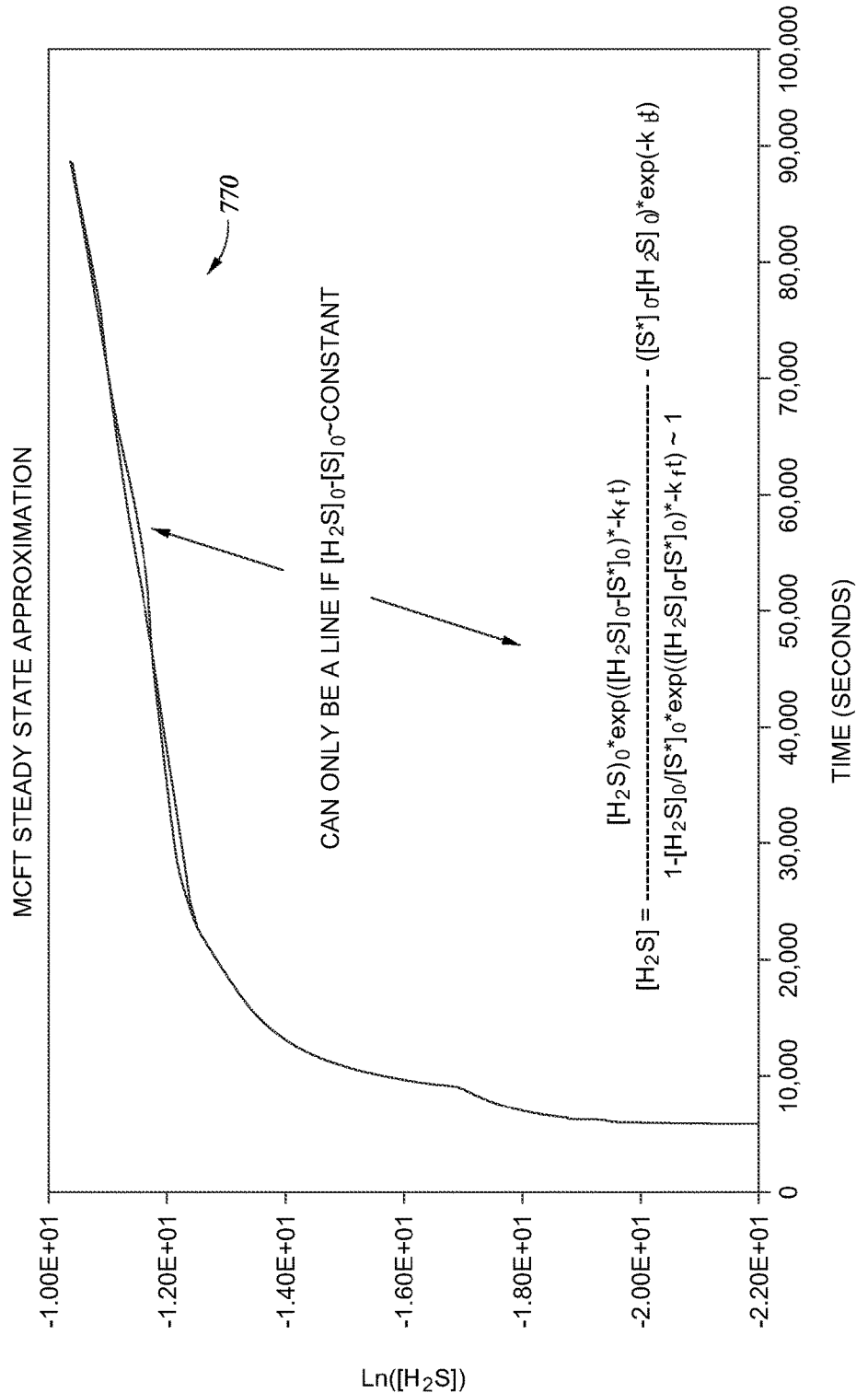
Figure 20:
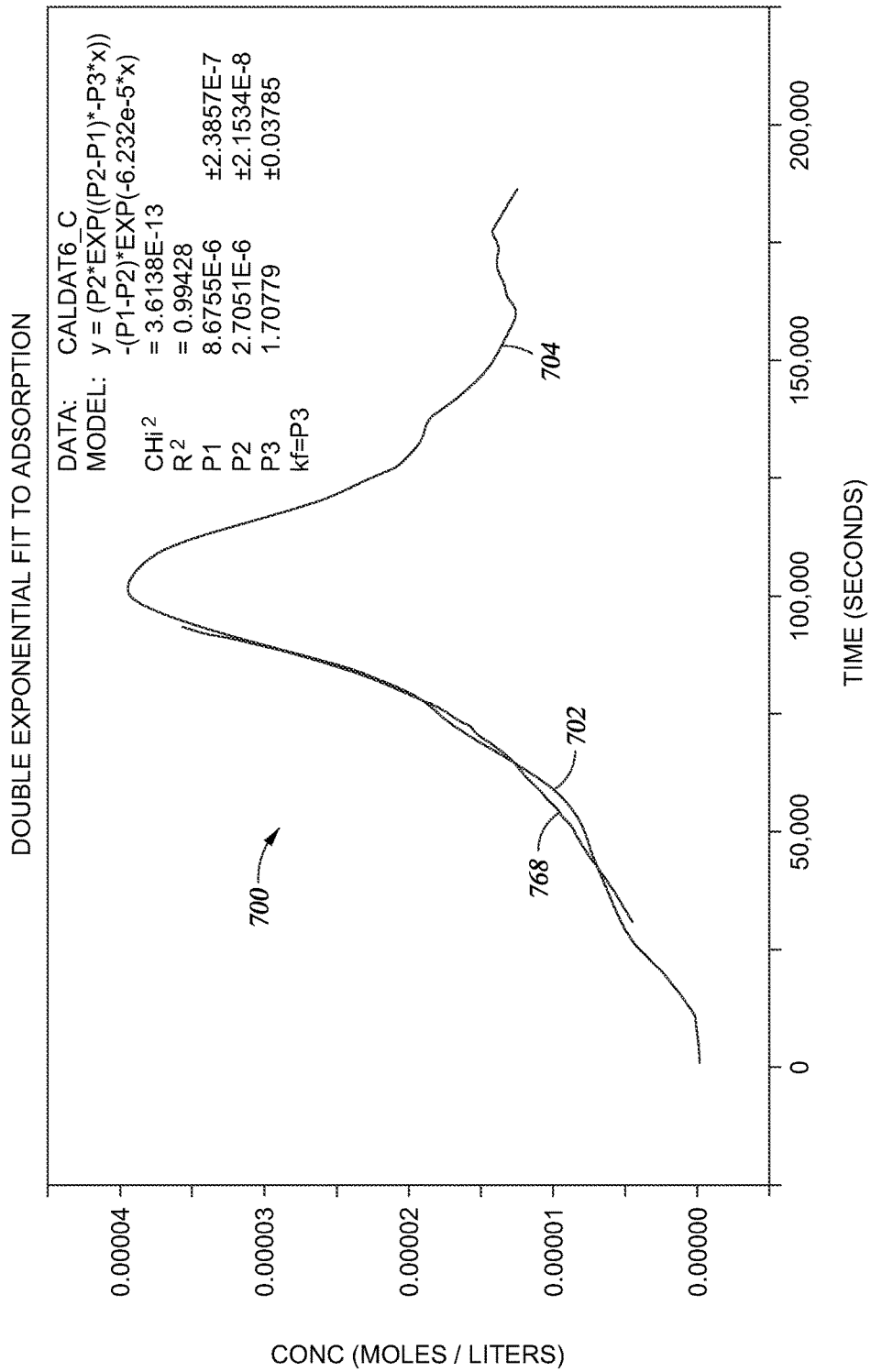
Figure 21:
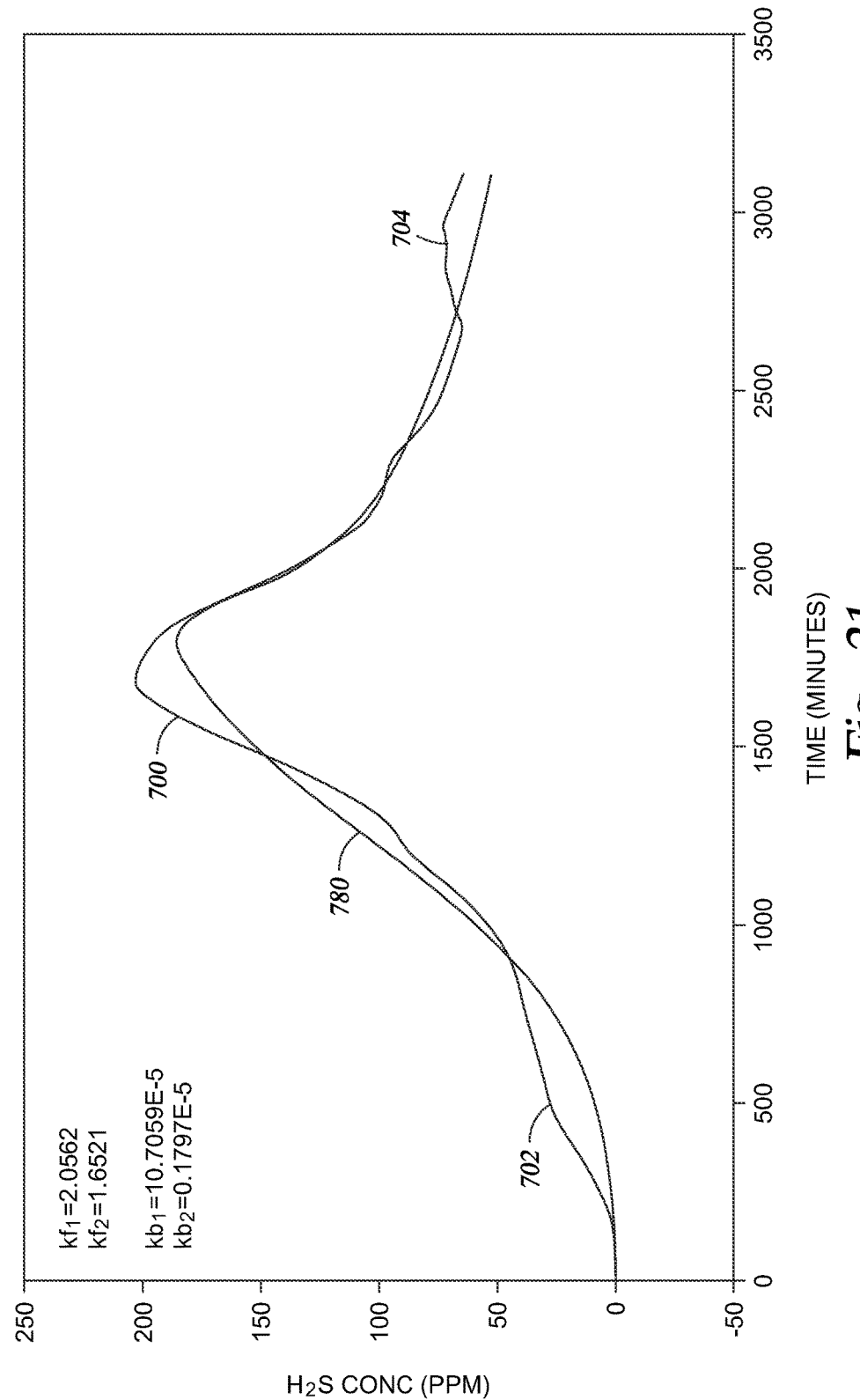

Next, and with reference to FIG. 18, the $H_2S$ simulation is initialized by first executing an exponential decay fit 766 to the desorption curve 704 of the $H_2S$ profile 700. Then, as shown in FIG. 19, a steady state approximation 770 is executed for the minimum configuration formation tester (MCFT). A double exponential fit 768 to the adsorption curve 702 of the $H_2S$ profile 700 is executed, as shown by FIG. 20. Finally, the test data curve 700 is compared to the simulation curve 780, as shown in FIG. 21. Such a comparison between the $H_2S$ simulated profile and the actual test data profile can be used to correct a downhole measurement of the $H_2S$ or other adsorbing chemical to actual concentration levels.

For an accurate simulation of $H_2S$-tool interaction, one or more of the following data or criteria sets, in various combinations, may be obtained and used: the forward (adsorption) and reverse (desorption) rate constants for materials within an exemplary formation tester section having $H_2S$ interaction responses, and the model of such $H_2S$ interaction; the active concentration of those $H_2S$ interactive materials within the formation tester section; the flow rate of fluid through the formation tester; the main state conditions (e.g., temperature, pressure, composition, etc.) within the formation tester or coupled modules; the inner geometry of the formation tester or module sections; and the expected concentration of $H_2S$ in the reservoir. In some embodiments, at least one measurement of the $H_2S$ concentration at the start of the sample flow operation can be used. In some embodiments, various combinations including less than all of the above listed simulation inputs will produce acceptable simulations of the experimental collected data by making assumptions about one or more of the simulation inputs.

In the embodiments disclosed, a MWD, LWD, sampling while drilling, wireline sampling, or wireline measurement tool is used to provide a model or simulation to help plan and execute an accurate sampling or measurement job with respect to $H_2S$ or other adsorbing chemical in the reservoir. A method as disclosed herein uses the $H_2S$ modeling or simulation to extrapolate $H_2S$ measurements either from downhole sensor measurements within the tool or from a captured sample to actual reservoir levels. A method as disclosed herein correlates one or more $H_2S$ measurements from downhole to actual reservoir levels. As described herein, a simulator is developed to describe actual $H_2S$-tool interaction, and the developed simulator is then used to predict or plan a sampling job with respect to $H_2S$. The sampling or measurement job can be modified in real time based on the simulator and collected $H_2S$ data, or the $H_2S$ measurements can be correlated to reservoir levels.

Figure 22:
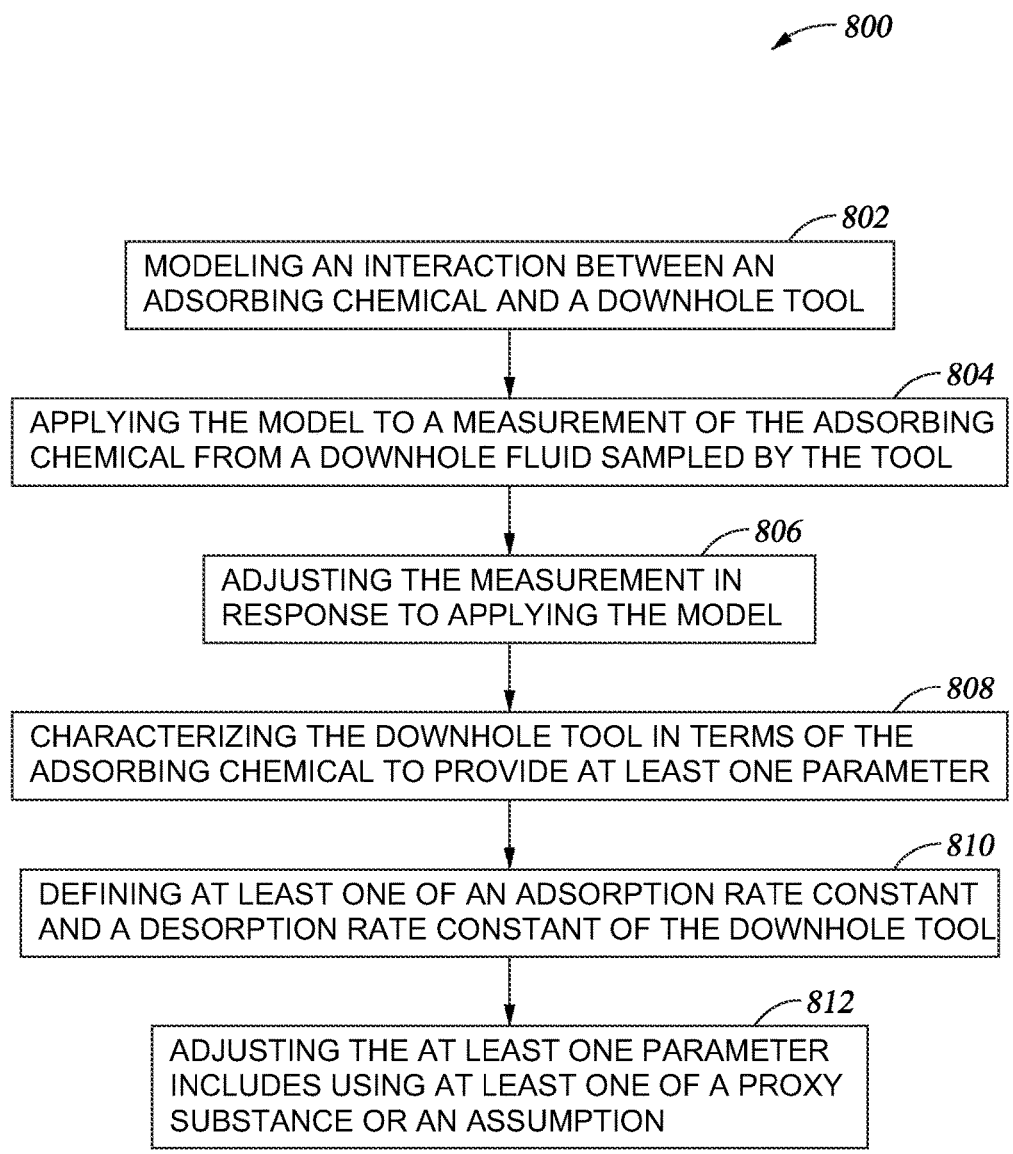
FIGS. 22-25 show various flow diagrams for embodiments of a method for measuring and adjusting an adsorbing chemical in downhole fluids according to the principles presented herein.

With reference to FIG. 22, one embodiment of a method 800 for adjusting the measurement of an adsorbing chemical in a subterranean well includes modeling an interaction between the adsorbing chemical and a downhole tool 802, applying the model to a measurement of the adsorbing chemical from a downhole fluid sampled by the tool 804, and adjusting the measurement in response to applying the model 806. In further embodiments, the modeling includes characterizing the downhole tool in terms of the adsorbing chemical to provide at least one parameter 808. The characterizing the downhole tool may include defining at least one of an adsorption rate constant and a desorption rate constant of the downhole 810, and a surface area of the downhole tool. The downhole tool may include multiple tool sections coupled together. In some embodiments, the method includes adjusting the at least one parameter using at least one of a proxy substance or an assumption 812. The above steps of the method can be performed in various orders and in various combinations that depart from the exact ordering and number of steps as described or shown.

Figure 23:
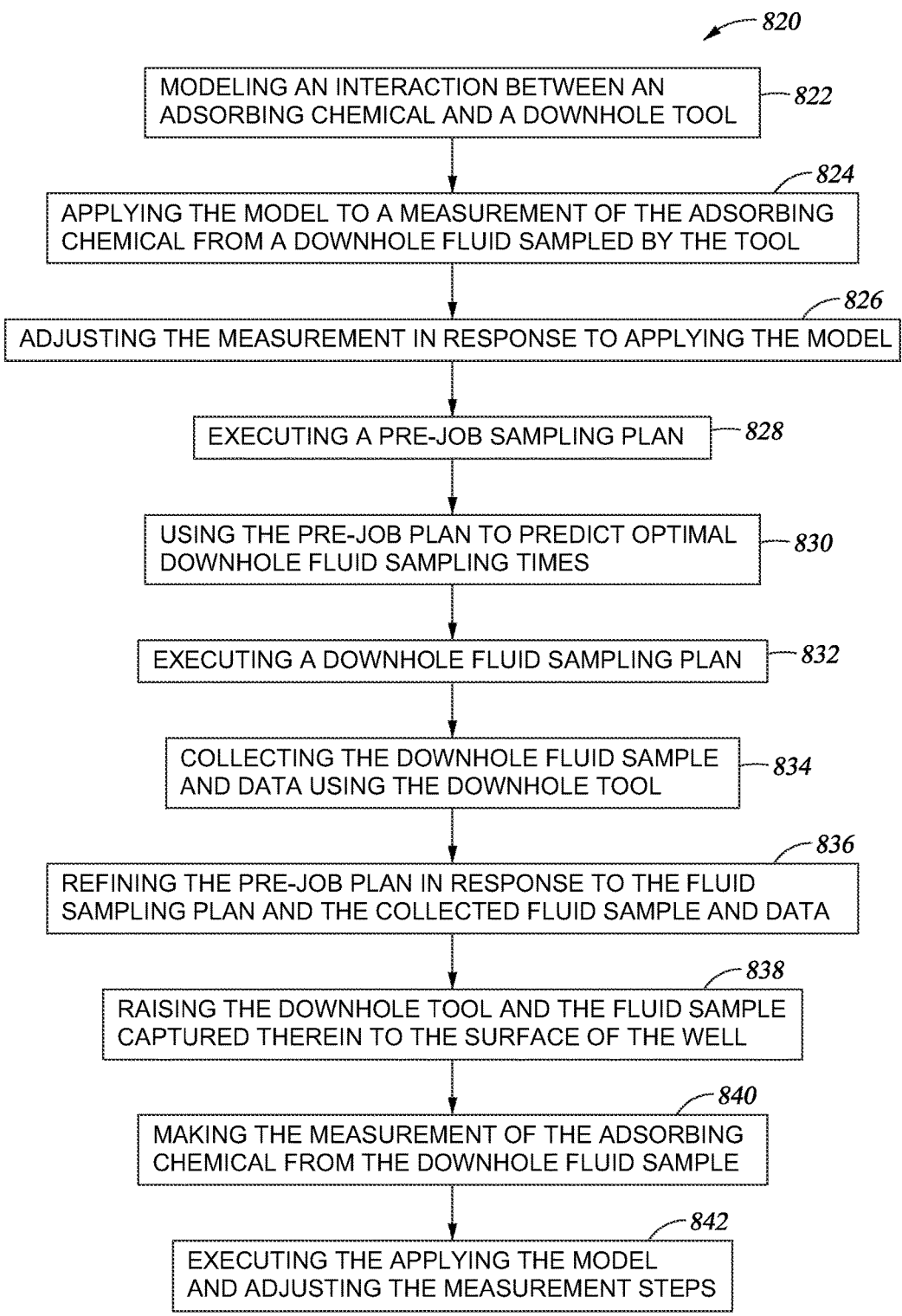

Referring to FIG. 23, another embodiment of a method 820 for adjusting the measurement of an adsorbing chemical in a subterranean well includes modeling an interaction between the adsorbing chemical and a downhole tool 822, applying the model to a measurement of the adsorbing chemical from a downhole fluid sampled by the tool 824, adjusting the measurement in response to applying the model 826, executing a pre job sampling plan 828 and using the pre job plan to predict optimal downhole fluid sampling times 830, executing a downhole fluid sampling plan 832 and collecting the downhole fluid sample and data using the downhole tool 834, refining the pre job plan in response to the fluid sampling plan and the collected fluid sample and data 836, raising the downhole tool and the fluid sample captured therein to the surface of the well 838, then making the measurement of the adsorbing chemical from the downhole fluid sample 840 and executing the applying the model and adjusting the measurement steps 842. In some embodiments, the method includes adjusting the model while the tool is downhole, wherein the measurement of the adsorbing chemical from the downhole fluid sample is made by at least one sensor in the downhole tool, and measuring a desorption rate of the downhole tool. The above steps of the method can be performed in various orders and in various combinations that depart from the exact ordering and number of steps as described or shown.

In some embodiments, the adsorbing chemical is a scaling or de-scaling chemical delivered to the well prior to applying the model, the downhole tool is part of a production string and includes a sensor for measuring the scaling or de-scaling chemical, the adsorbing chemical is a tracer delivered to the well prior to applying the model, and/or the downhole tool is a fluid sampler or a coring tool for obtaining the tracer. In some embodiments, the tracer includes at least one of a filtrate tracer, a radioactive tracer, Tritium, a bromide compound, an iodide compound, a fatty acid, Nitrate anion, or other tracers used in the industry.

Figure 24:
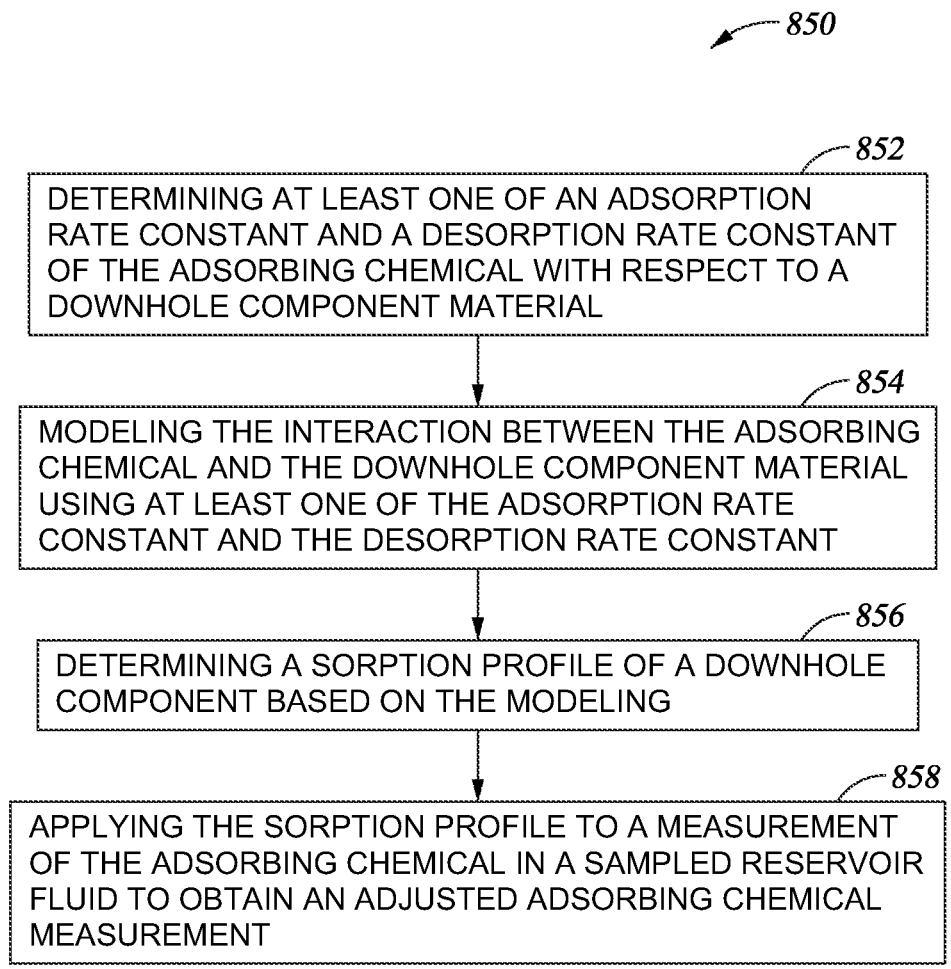

Referring to FIG. 24, an embodiment of a method 850 for measuring an adsorbing chemical in a subterranean reservoir includes determining at least one of an adsorption rate constant and a desorption rate constant of the adsorbing chemical with respect to a downhole component material 852, modeling the interaction between the adsorbing chemical and the downhole component material using at least one of the adsorption rate constant and the desorption rate constant 854, determining a sorption profile of a downhole component based on the modeling 856, and applying the sorption profile to a measurement of the adsorbing chemical in a sampled reservoir fluid to obtain an adjusted adsorbing chemical measurement 858.

In further embodiments of the method 850, the method may include one of the following features or actions, or combinations thereof: wherein determining at least one of the adsorption rate constant and the desorption rate constant includes testing a downhole tool subsection by flowing the adsorbing chemical through the tool subsection; wherein determining at least one of the adsorption rate constant and the desorption rate constant includes testing multiple downhole tool subsections coupled together by flowing the adsorbing chemical through the coupled subsections; measuring a concentration of the adsorbing chemical as a function of time; comparing the adsorbing chemical measurements to a finite steady state model; wherein the modeling further includes determining a surface area of a downhole tool component; wherein the determining the surface area of the downhole tool component includes assuming the surface area; wherein the determining the surface area of the downhole tool component includes characterizing the surface area using time data, component wear data, and increased surface area data; wherein the determining the surface area of the downhole tool component includes using a proxy substance; wherein the applying the model to obtain the adjusted adsorbing chemical measurement occurs downhole; and wherein the adsorbing chemical is at least one of $H_2S$, $CO_2$, Mercury, a tracer, a water-scaling chemical, a sulfur-containing species, or a mercaptian. In some embodiments, the tracer includes at least one of a filtrate tracer, a radioactive tracer, Tritium, a bromide compound, an iodide compound, a fatty acid, Nitrate anion, or other tracers used in the industry.

Figure 25:
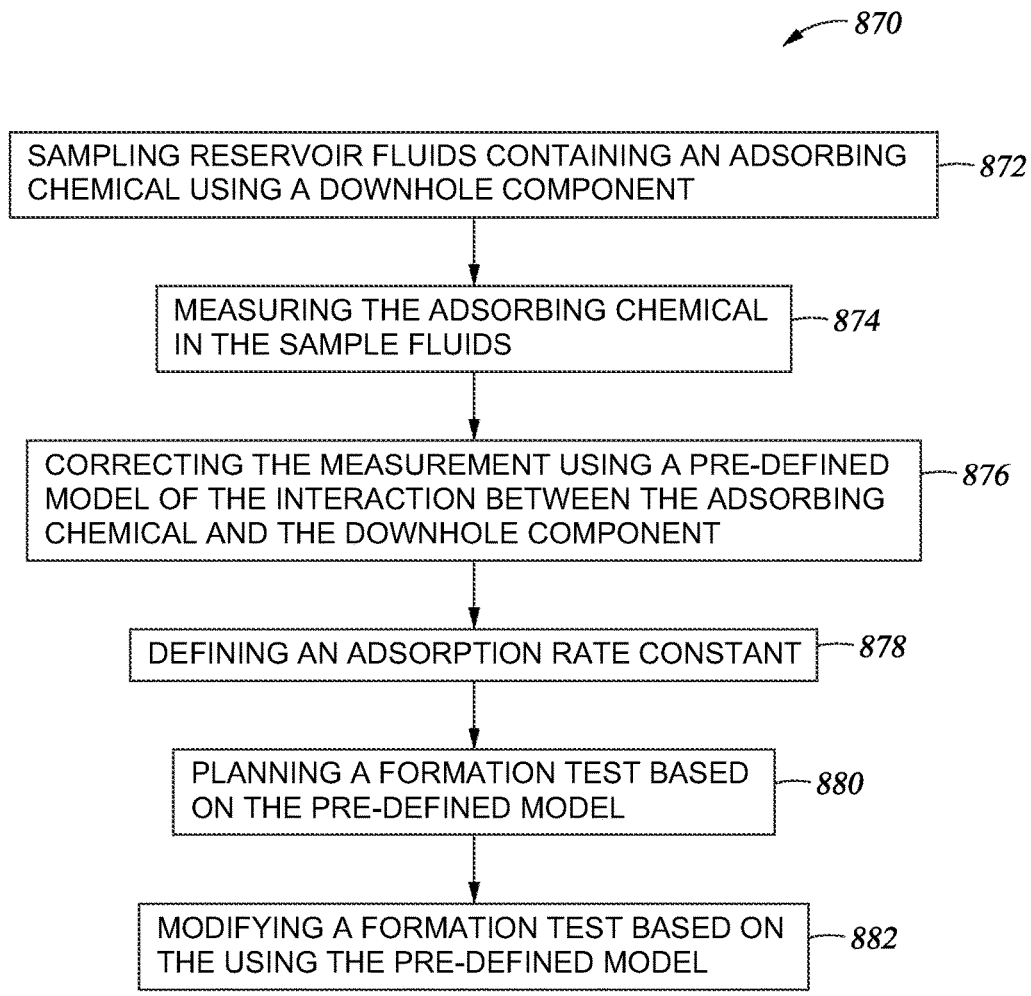

Referring to FIG. 25, an embodiment of a method 870 of sampling fluids in a subterranean reservoir includes sampling reservoir fluids containing an adsorbing chemical using a downhole component 872, measuring the adsorbing chemical in the sampled fluids 874, and correcting the measurement using a pre-defined model of the interaction between the adsorbing chemical and the downhole component 876. In further embodiments, the method includes defining an adsorption rate constant 878, defining a desorption rate constant 880, planning a formation test based on the pre-defined model 882, and modifying a formation test based on the using the pre-defined model 884. In further embodiments, the adsorbing chemical is $H_2S$, the corrected measurement is an estimation of the actual level of the adsorbing chemical in the reservoir fluids, the defining includes simulating interaction of the adsorbing chemical with an interactive material of the downhole component, the model includes defining a surface area of the downhole component, and the method includes developing a well plan based on the using the pre-defined model.

An embodiment of the method includes developing a simulation model adapted to describe variable tool configuration and/or geometry, obtaining the rate constants for the $H_2S$ interactive tool materials for the model (in various embodiments, the rate constants may be obtained by one or more of literature searches, experimentation, or reasonable assumptions or approximations), configuring a tool for a desired job and the associated simulation variation, using expected conditions (in various embodiments, the conditions may be one or more of temperature, pressure, flow rate) and the maximum, minimum, and mid-range expected $H_2S$ concentrations, or an appropriate combination of one or more of the listed $H_2S$ ranges to simulate the $H_2S$ profile for the tool, planning the sampling or testing job using the gained knowledge of the $H_2S$-tool interaction, updating the simulation to provide more control over the $H_2S$ sampling capability as parameters change during sampling, or more accurate information becomes available (in various embodiments, the updated information includes one or more of temperature, pressure, or flow rate), using one or more $H_2S$ concentration points, as they become available during sampling, to constrain the simulation for more accurate behavior prediction (or, in some embodiments, using the information to back-simulate (history match) an accurate representation of $H_2S$ in the reservoir), assigning a confidence that the $H_2S$ measured in the sample chamber matches the $H_2S$ in the reservoir (or, in some embodiments, back-simulate the amount of $H_2S$ that must have been present in the reservoir to obtain the sample captured and measured), and using the current passivation level of $H_2S$ as a starting point for the updated planning of the next job, if another sampling job is to occur prior to full desorption of the tool.

Exemplary information provide by the simulation embodiments described herein to help plan the sampling job include: a minimum time that the tool must be flushed to capture an accurate $H_2S$ sample representative of the reservoir, a maximum time that the tool must be flushed to capture an accurate $H_2S$ sample representative of the reservoir, a minimum time that the tool must be flushed to begin to sample any $H_2S$, a maximum time that the tool must be flushed to begin to sample any $H_2S$, an expected time vs. sampled $H_2S$ profile so that an operator may choose to sample at 80% $H_2S$, 60% $H_2S$, or any other chosen level of $H_2S$ reservoir concentration that yields desirable results, a minimum time that the tool must be flushed to capture an $H_2S$ sample that can be extrapolated to the reservoir concentration, a maximum time that the tool must be flushed to capture an H$_2$S sample that can be extrapolated to the reservoir concentration, a confidence of extrapolation for a captured H$_2$S sample that can be extrapolated to the reservoir concentration as a function of time, and a time necessary for desorption of H$_2$S from the tool if the subsequent section of reservoir has a lower concentration of H$_2$S than the previously sampled section of reservoir.

In exemplary embodiments of the method for measuring an adsorbing chemical in a subterranean well or reservoir, the method includes determining at least one of an adsorption rate constant and a desorption rate constant of the adsorbing chemical with respect to a downhole component material, modeling the interaction between the adsorbing chemical and the downhole component material using at least one of the adsorption rate constant and the desorption rate constant, and applying the model to a measurement of the adsorbing chemical in a sampled reservoir fluid to obtain an adjusted adsorbing chemical measurement. The method may also include determining a sorption profile of a downhole component. The method may include determining at least one of the adsorption rate constant and the desorption rate constant comprises testing a downhole tool subsection by flowing the adsorbing chemical through the tool subsection. The method may include determining at least one of the adsorption rate constant and the desorption rate constant comprises testing multiple downhole tool subsections coupled together by flowing the adsorbing chemical through the coupled subsections.

The method may further include measuring a concentration of the adsorbing chemical as a function of time, then comparing the adsorbing chemical measurements to a finite steady state model. The modeling of the method may include determining a surface area of a downhole tool component, wherein determining the surface area of the downhole tool component includes assuming the surface area, characterizing the surface area using time data, component wear data, and increased surface area data, or using a proxy substance. Applying the model to obtain the adjusted adsorbing chemical measurement may occur downhole in some embodiments.

In exemplary embodiments of the method for adjusting the measurement of an adsorbing chemical in a subterranean well includes modeling interaction between the adsorbing chemical and a downhole tool, applying the model to a measurement of the adsorbing chemical from a downhole fluid sampled by the tool, and adjusting the measurement in response to applying the model. The adsorbing chemical may be a scaling or de-scaling chemical delivered to the well prior to applying the model, and the downhole tool may be part of a production string and include a sensor for measuring the scaling or de-scaling chemical. The adsorbing chemical may be a tracer delivered to the well prior to applying the model, and the downhole tool may be a fluid sampler or a coring tool for obtaining the tracer. In some embodiments, the tracer includes at least one of a filtrate tracer, a radioactive tracer, Tritium, a bromide compound, an iodide compound, a fatty acid, Nitrate anion, or other tracers used in the industry.

The modeling of the method may include characterizing the downhole tool in terms of the adsorbing chemical to provide at least one parameter. The parameter(s) and the characterizing of the downhole tool may include defining at least one of an adsorption rate constant and a desorption rate constant of the downhole, and a surface area of the downhole tool. The downhole tool may include multiple tool sections coupled together. The parameter(s) may be adjusted using at least one of a proxy substance or an assumption.

The method may further include executing a pre job sampling plan and using the pre job plan to predict optimal downhole fluid sampling times. Also, the method may include executing a downhole fluid sampling plan and collecting the downhole fluid sample and data using the downhole tool. The pre-job plan may be refined in response to the fluid sampling plan and the collected fluid sample and data.

In some embodiments, the method includes raising the downhole tool and the fluid sample captured therein to the surface of the well, then making the measurement of the adsorbing chemical from the downhole fluid sample and executing the applying the model and adjusting the measurement steps.

The model may be adjusted while the tool is downhole. The measurement of the adsorbing chemical from the downhole fluid sample may be made by at least one sensor in the downhole tool. Further, the desorption rate of the downhole tool may be measure accordingly.

In exemplary embodiments, a method of sampling fluids in a subterranean reservoir includes sampling reservoir fluids containing an adsorbing chemical using a downhole component, measuring the adsorbing chemical in the sampled fluids, and correcting the measurement using a pre-defined model of the interaction between the adsorbing chemical and the downhole component. The corrected measurement may be an estimation of the actual level of the adsorbing chemical in the reservoir fluids. The model may include defining an adsorption rate constant. The adsorption rate constant may be defined by simulating interaction of the adsorbing chemical with an interactive material of the downhole component. The model may include defining a desorption rate constant. The model may include defining a surface area of the downhole component.

In some of the methods, planning a formation test based on the pre-defined model is executed. The method may include developing a well plan based on the using the pre-defined model. The method may include modifying a formation test based on the using the pre-defined model.

A system for sampling fluids including an adsorbing chemical in a subterranean reservoir includes a formation tester as described herein, coupled to a processor as described with respect to FIGS. 1-3, and wherein the processor is configured to perform the various steps as disclosed throughout the present disclosure. For example, the formation tester may include a sorption profile based on a modeling of the interaction between an adsorbing chemical and the formation tester using at least one of an adsorption rate constant and a desorption rate constant. The processor may be configured to apply the sorption profile to a measurement of the adsorbing chemical in a sampled formation fluid as taken by the formation tester to obtain an adjusted adsorbing chemical measurement.

The embodiments set forth herein are merely illustrative and do not limit the scope of the disclosure or the details therein. It will be appreciated that many other modifications and improvements to the disclosure herein may be made without departing from the scope of the disclosure or the inventive concepts herein disclosed. Because many varying and different embodiments may be made within the scope of the inventive concept herein taught, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A method of sampling fluids including an adsorbing chemical in a subterranean reservoir comprising: using a computer processor, modeling a chemical interaction between an adsorbing chemical and a downhole tool; deploying the downhole tool into a borehole of a well extending along a reservoir; using the downhole tool, sampling a downhole fluid sample containing the adsorbing chemical; using the computer processor, applying the model to a measurement of the adsorbing chemical in the downhole fluid sample while the downhole tool is in the borehole; and using the computer processor, adjusting the measurement of the adsorbing chemical in response to applying the model.

2. The method of claim 1 wherein the modeling comprises characterizing the downhole tool in terms of the adsorbing chemical to provide at least one parameter.

3. The method of claim 2 wherein the characterizing the downhole tool comprises defining at least one of an adsorption rate constant and a desorption rate constant of the downhole tool, and a surface area of the downhole tool.

4. The method of claim 1 further comprising:
executing a pre-job sampling plan; and
using the pre-job plan to predict optimal downhole fluid sampling times.

5. The method of claim 4 further comprising:
executing a downhole fluid sampling plan; and
collecting the downhole fluid sample and data using the downhole tool.

6. The method of claim 5 further comprising refining the pre-job plan in response to the fluid sampling plan and the collected fluid sample and data.

7. The method of claim 5 further comprising:
raising the downhole tool and the fluid sample captured therein to the surface of the well;
then making the measurement of the adsorbing chemical from the downhole fluid sample; and
executing the applying the model and adjusting the measurement steps.

8. The method of claim 1 further comprising adjusting the model while the tool is downhole.

9. The method of claim 1 wherein the adsorbing chemical is a scaling or de-scaling chemical delivered to a well prior to applying the model, and wherein the downhole tool is part of a production string and includes a sensor for measuring the scaling or de-scaling chemical.

10. The method of claim 1 wherein the adsorbing chemical is a tracer delivered to a well prior to applying the model, and wherein the downhole tool is a fluid sampler or a coring tool for obtaining the tracer.

11. The method of claim 10 wherein the tracer comprises at least one of a filtrate tracer, a radioactive tracer, Tritium, a bromide compound, an iodide compound, a fatty acid, and Nitrate anion.

12. A method of sampling fluids including an adsorbing chemical in a subterranean reservoir comprising: using a computer processor, determining at least one of an adsorption rate constant and a desorption rate constant of an adsorbing chemical with respect to a downhole component material; using the computer processor, modeling a chemical interaction between the adsorbing chemical and the downhole component material using at least one of the adsorption rate constant and the desorption rate constant; using the computer processor, determining a sorption profile of a downhole component based on the modeling; deploying a downhole tool into a borehole of a well extending along a reservoir; using the downhole tool, sampling reservoir fluid containing the adsorbing chemical; and using the computer processor, applying the sorption profile to a measurement of the adsorbing chemical in the sampled reservoir fluid while the downhole tool is in the borehole to obtain an adjusted adsorbing chemical measurement of the adsorbing chemical.

13. The method of claim 12 wherein determining at least one of the adsorption rate constant and the desorption rate constant comprises testing a downhole tool subsection by flowing the adsorbing chemical through the tool subsection.

14. The method of claim 12 wherein determining at least one of the adsorption rate constant and the desorption rate constant comprises testing multiple downhole tool subsections coupled together by flowing the adsorbing chemical through the coupled subsections.

15. The method of claim 13 further comprising measuring a concentration of the adsorbing chemical as a function of time.

16. The method of claim 15 further comprising comparing the adsorbing chemical measurements to a finite steady state model.

17. The method of claim 12 wherein the modeling further comprises determining a surface area of a downhole tool component.

18. The method of claim 12 wherein the applying the model to obtain the adjusted adsorbing chemical measurement occurs downhole.

19. The method of claim 12 wherein the adsorbing chemical is at least one of $H_2S$, $CO_2$, Mercury, a tracer, a water-scaling chemical, a sulfur-containing species, or a mercaptian.

20. The method of claim 19 wherein the tracer comprises at least one of a filtrate tracer, a radioactive tracer, Tritium, a bromide compound, an iodide compound, a fatty acid, and Nitrate anion.

21. A method of sampling fluids including an adsorbing chemical in a subterranean reservoir comprising: deploying a downhole tool into a borehole of a well extending along a reservoir; sampling reservoir fluids containing an adsorbing chemical using a downhole component of the downhole tool; using a computer processor, measuring the adsorbing chemical in the sampled fluids; and using the computer processor, correcting the measurement of the adsorbing chemical using a pre-defined model of a chemical interaction between the adsorbing chemical and the downhole component while the downhole tool is in the borehole.

22. The method of claim 21 wherein the adsorbing chemical is $H_2S$.

23. The method of claim 21 wherein the corrected measurement is an estimation of the actual level of the adsorbing chemical in the reservoir fluids.

24. The method of claim 21 wherein the model comprises defining an adsorption rate constant.

25. The method of claim 24 wherein the defining comprises simulating interaction of the adsorbing chemical with an interactive material of the downhole component.

26. The method of claim 24 wherein the model comprises defining a desorption rate constant.

27. The method of claim 24 wherein the model comprises defining a surface area of the downhole component.

28. The method of claim 21 further comprising planning a formation test based on the pre-defined model.

29. The method of claim 21 further comprising developing a well plan based on the using the pre-defined model.

30. The method of claim 21 further comprising modifying a formation test based on the using the pre-defined model.

31. A system for sampling fluids including an adsorbing chemical in a subterranean reservoir comprising: a formation tester including a sorption profile based on a modeling of a chemical interaction between an adsorbing chemical and the formation tester using at least one of an adsorption rate constant and a desorption rate constant; and a processor coupled to the formation tester to apply the sorption profile to a measurement of the adsorbing chemical in a sampled formation fluid to obtain an adjusted adsorbing chemical measurement while the formation tester is positioned in a borehole extending along the reservoir.

* * * * *